United States Patent [19]

Civelli et al.

[11] Patent Number: 5,422,265

[45] Date of Patent: Jun. 6, 1995

[54] DNA SEQUENCE FOR THE HUMAN DOPAMINE RECEPTOR D4 AND EXPRESSION THEREOF IN MAMMALIAN CELLS

[75] Inventors: Olivier Civelli, Portland, Oreg.; Hubert H. Van Tol, Toronto, Canada

[73] Assignee: State of Oregon, Acting by and Through the State Board of Higher Education on Behalf of the Oregon Health Sciences University, Portland, Oreg.

[21] Appl. No.: 626,618

[22] Filed: Dec. 7, 1990

[51] Int. Cl.$^6$ .................. C12N 1/20; C12N 15/00; C07H 17/00; C12Q 1/68

[52] U.S. Cl. .................. 435/252.3; 435/320.1; 435/6; 536/23.5; 935/22; 935/34; 935/1

[58] Field of Search .................. 536/27, 23.5, 24.31; 435/320.1, 240.1, 91; 935/1, 34, 11, 12, 22, 24, 77

[56] References Cited

PUBLICATIONS

Cooper et al., The Biochemical Basis of Neuropharmacology, 3d ed. 1978 (Oxford University Press; N.Y.), pp. 161-195.
Kebabian and Calne, Nature 277; 93-96 (1979).
Senogles et al., Biochemistry 25: 749-753 (1986).
Sengoles et al., J. Biol. Chem. 263: 18996-19002 (1988).
Gingrich et al., J. Biochemistry 27: 3907-3912 (1988).
Amlaiky et al., Mol. Pharmacol. 31: 129-134 (1987).
Ninik et al., Biochemistry 27: 7594-7599 (1988).
Amlaiky and Caron, J. Biol. Chem. 260: 1983-1986 (1985).
Amlaiky and Caron, J. Neurochem. 47: 196-204 (1986).
Jarvie et al., Mol. Pharmacol. 34: 91-97 (1988).
Sokoloff et al., Nature 347: 146-151 (1990).
Seeman et al., Neuropyschopharm. 1: 5-15 (1987).
Seeman, Synapse 1: 133-152 (1987).
Bunzow et al., Nature 336: 783-787 (1988).
Grandy et al., Proc. Natl. Acad. Sci. U.S.A. 86: 9762-9766 (1989).
Dal Toso et al., EMBO J. 8: 4025-4034 (1989).
Zhou et al., Nature 347: 76-80 (1990).
Sunahara et al., Nature 347: 80-83 (1990).
Kane et al., Arch. Gen. Psychiat. 45: 789-796 (1988).
Casey, Psychopharmacology 99: S47-S53 (1989).
Ackenheil et al., Arzneim-Forsch 26: 1156-1158 (1976).
Sandoz Canada, Inc., Clozaril: Summary of preclinical and clincal data (1990).
Dohlman et al., Biochemistry 26: 2657-2664 (1987).
Davis et al. "Efficient Isolation of Genes by Using Antibody Probes", P.N.A.S., U.S.A., vol. 80, pp. 1194-1198, Mar. 1983.
Sanger et al., "DNA Sequencing with Chain-Terminating Inhibitors", P.N.A.S., U.S.A., vol. 74, No. 12, pp. 5463-5467, Dec. 1977.
Sommer, et al., *Nucleic Acids Research*, vol. 17, No. 16, 1989, p. 6749.

Primary Examiner—Margaret Parr
Assistant Examiner—Bradley L. Sisson
Attorney, Agent, or Firm—Allegretti & Witcoff

[57] ABSTRACT

The present invention is directed toward the human D4 dopamine receptor. The nucleotide sequence of the gene corresponding to this receptor is provided by the invention. The invention also includes a recombinant eukaryotic expression vector capable of expressing the human D4 dopamine receptor in cultures of transformed eukaryotic cells and such cultures of transformed eukaryotic cells which synthesize the human D4 dopamine receptor.

3 Claims, 13 Drawing Sheets

FIG. 2

```
5'-CGGGGGCGGGACCAGGGTCCGGCCGGGGCGTGCCCCC
GGGGAGGGACTCCCCGGCTTGCCCCCGGCGTTGTCCGCGGTG
                          +1
CTCAGCGCCCGCCCGGGCGCGCC ATG GGG AAC CGC AGC
                        MET GLY ASN ARG SER
                                            48
ACC GCG GAC GCG GAC GGG CTG CTG GCT GGG CGC
THR ALA ASP ALA ASP GLY LEU LEU ALA GLY ARG
                                ▲
GGG CGG GCC GCG GGG GCA TCT GCG GGG GCA TCT
GLY PRO ALA ALA GLY ALA SER ALA GLY ALA SER
                                            114
GCG GGG CTG GCT GGG CAG GGC GCG GCG GCG CTG
ALA GLY LEU ALA GLY GLN GLY ALA ALA ALA LEU

GTG GGG GGC GTG CTG CTC ATC GGC GCG GTG CTC
VAL GLY GLY VAL LEU LEU ILE GLY ALA VAL LEU
                                            180
GCG GGG AAC TCG CTC GTG TGC GTG AGC GTG GCC
ALA GLY ASN SER LEU VAL CYS VAL SER VAL ALA

ACC GAG CGC GCC CTG CAG ACG CCC ACC AAC TCC
THR GLU ARG ALA LEU GLN THR PRO THR ASN SER
                                            246
TTC ATC GTG AGC CTG GCG GCC GCC GAC CTC CTC
PHE ILE VAL SER LEU ALA ALA ALA ASP LEU LEU

CTC GCT CTC CTG GTG CTG CCG CTC TTC GTC TAC
LEU ALA LEU LEU VAL LEU PRO LEU PHE VAL TYR

TCC GAG GTGAGCCGCGTCCGGCCGCA...............
SER GLU

...CCTGTGGTGTCGCCGCGCAG GTC CAG GGT GGC GCG
                        VAL GLN GLY GLY ALA
                                            333
TGG CTG CTG AGC CCC CGC CTG TGC GAC GCC CTC
TRP LEU LEU SER PRO ARG LEU CYS ASP ALA LEU
```

FIG. 2 cont.

```
ATG GCC ATG GAC GTC ATG CTG TGC ACC GCC TCC
MET ALA MET ASP VAL MET LEU CYS THR ALA SER
                                            398
ATC TTC AAC CTG TGC GCC ATC AGC GTG GAC AG
ILE PHE ASN LEU CYS ALA ILE SER VAL ASP ARG

GTGCCGCCCTCCCCGCCCGCGCCCCGGCGCCCCGCGCCCC

GCCGCCGCCCTCACCGCGGCCTGTGCGCTGTCCGGCGCCCCC

TCGGCGCTCCCCGCAG   G TTC GTG GCC GTG GCC GTG
                     PHE VAL ALA VAL ALA VAL
                                             450
CCG CTG CGC TAC AAC CGG CAG GGT GGG AGC CGC
PRO LEU ARG TYR ASN ARG GLN GLY GLY SER ARG

CGG CAG CTG CTG CTC ARC GGC GCC ACG TGG CTG
ARG GLN LEU LEU LEU ILE GLY ALA THR TRP LEU
                                          □ 516
CTG TCC GCG GCG GTG GCG GCG CCC GTA CTG TGC
LEU SER ALA ALA VAL ALA ALA PRO VAL LEU CYS

GGC CTC AAC GAC GTG CGC GGC CGC GAC CCC GCC
GLY LEU ASN ASP VAL ARG GLY ARG ASP PRO ALA
                                            582
GTG TGC CGC CTG GAG GAC CGC GAC TAC GTG GTC
VAL CYS ARG LEU GLU ASP ARG ASP TYR VAL VAL

TAC TCG TCC GTG TGC TCC TTC TTC CTA CCC TGC
TYR SER SER VAL CYS SER PHE PHE LEU PRO CYS
                                            648
CCG CTC ATG CTG CTG CTG TAC TGG GCC ACG TTC
PRO LEU MET LEU LEU LEU TYR TRP ALA THR PHE

CGC GGC CTG CAG CGC TGG GAG GTG GCA CGT CGC
ARG GLY LEU GLN ARG TRP GLU VAL ALA ARG ARG
                                            714
GCC AAG CTG CAC GGC CGC GCG CCC CGC CGA CCC
ALA LYS LEU HIS GLY ARG ALA PRO ARG ARG PRO
```

FIG. 2 cont.

```
AGC GGC CCT GGC CCG CCT TCC CCC ACG CCA CCC
SER GLY PRO GLY PRO PRO SER PRO THR PRO PRO
                                           780
GCG CCC CGC CTC CCC CAG GAC CCC TGC GGC CCC
ALA PRO ARG LEU PRO GLN ASP PRO CYS GLY PRO
GAC TGT GCG CCC CCG GCG CCC GGC CT TCCCCGGG
ASP CYS ALA PRO PRO ALA PRO GLY LEU
```

GTCCCTGCGGCC......CCTGTGCGCCCCCGCGCCCGGCCT

CCCCCAGGACCCCTGCGGCCCCGACTGTGCGCCCCCGCGCCC
                                        834
GGCCT C CCC CCG GAC CCC TGC GGC TCC AAC TGT
      PRO PRO ASP PRO CYS GLY SER ASN CYS

```
GCT CCC CCC GAC GCC GTC AGA GCC GCC GCG CTC
ALA PRO PRO ASP ALA VAL ARG ALA ALA ALA LEU
                                           900
CCA CCC CAG ACT CCA CCG CAG ACC CGC AGG AGG
PRO PRO GLN THR PRO PRO GLN THR ARG ARG ARG
CGG CGT GCC AAG ATC ACC GGC CGG GAG CGC AAG
ARG ARG ALA LYS ILE THR GLY ARG GLU ARG LYS
GCC ATG AGG GTC CTG CCG GTG GTG GTC G GTGG
ALA MET ARG VAL LEU PRO VAL VAL VAL
```

GTTCCTGTCCTGAGGGGCGGGGAGGAGAGGAGGGGGGGAGTAC

GAGGCCGGCTGGGCGGGGGGCGCTAACGCGGCTCTCGGCGCCC

CCAG GG GCC TTC CTG CTG TGC TGG ACG CCC TTC
     GLY ALA PHE LEU LEU CYS TRP THR PRO PHE
                                           1023
TTC GTG GTG CAC ATC ACG CAG GCG CTG TGT CCT
PHE VAL VAL HIS ILE THR GLN ALA LEU CYS PRO

FIG. 2 cont.

```
GCC TGC TCC GTG CCC CCG CGG CTG GTC AGC GCC
ALA CYS SER VAL PRO PRO ARG LEU VAL SER ALA
                                         1089
GTC ACC TGG CTG GGC TAC GTC AAC AGC GCC CTC
VAL THR TRP LEU GLY TYR VAL ASN SER ALA LEU

ACC CCC GTC ATC TAC ACT GTC TTC AAC GCC GAG
ASN PRO VAL ILE TYR THR VAL PHE ASN ALA GLU
                                         1155
TTC CGC AAC GTC TTC CGC AAG GCC CTG CGT GCC
PHE ARG ASN VAL PHE ARG LYS ALA LEU ARG ALA
    1164
TGC TGC TGA  GCCGGGCACCCCCGGACGCCCCCCGGCCTG
CYS CYS STOP

ATGGCCAGGCCTCAGGGACCAAGGAGATGGGGAGGGCGCTTTT

GTACGTTAATTAAACAAATTCCTTCCCAAACTCAGCTGTGAAG
                                AAAAAAAAAAAAAAAAAAA
GCTCCTGGG-3'
AA
```

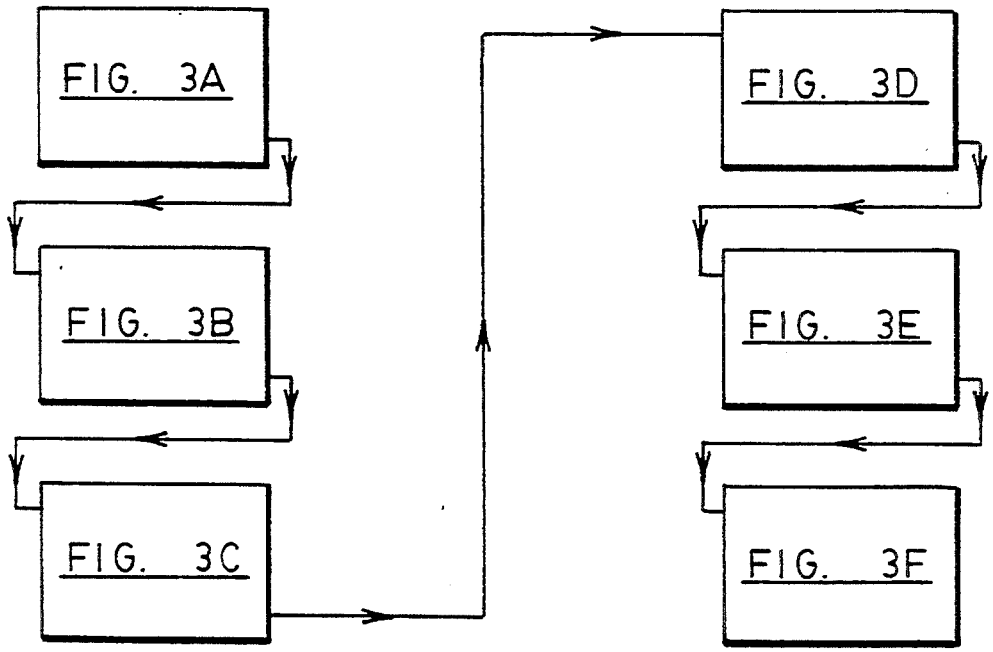

```
D1 HUMAN  P A T N N A I E T V S I N N N G A A M F S S H H E P R G S I S K
D1 RAT    P T T N N A I E T V S I N N N G A V F S S H H E P R G S I S K

D1 HUMAN  E C N L V Y L I P H A V G S S E D L K K E E A G G I A R P L E K
D1 RAT    D C N L V Y L I P H A V G S S E D L K K E E A G G I A K P L E K

D1 HUMAN  L S P A L S V I L D Y D T D V S L E K I Q P I T Q G Q H P T
D1 RAT    L S P A L S V I L D Y D T D V S L E K I Q P V T H S Q H S T

D1 HUMAN  446
D1 RAT    446
```

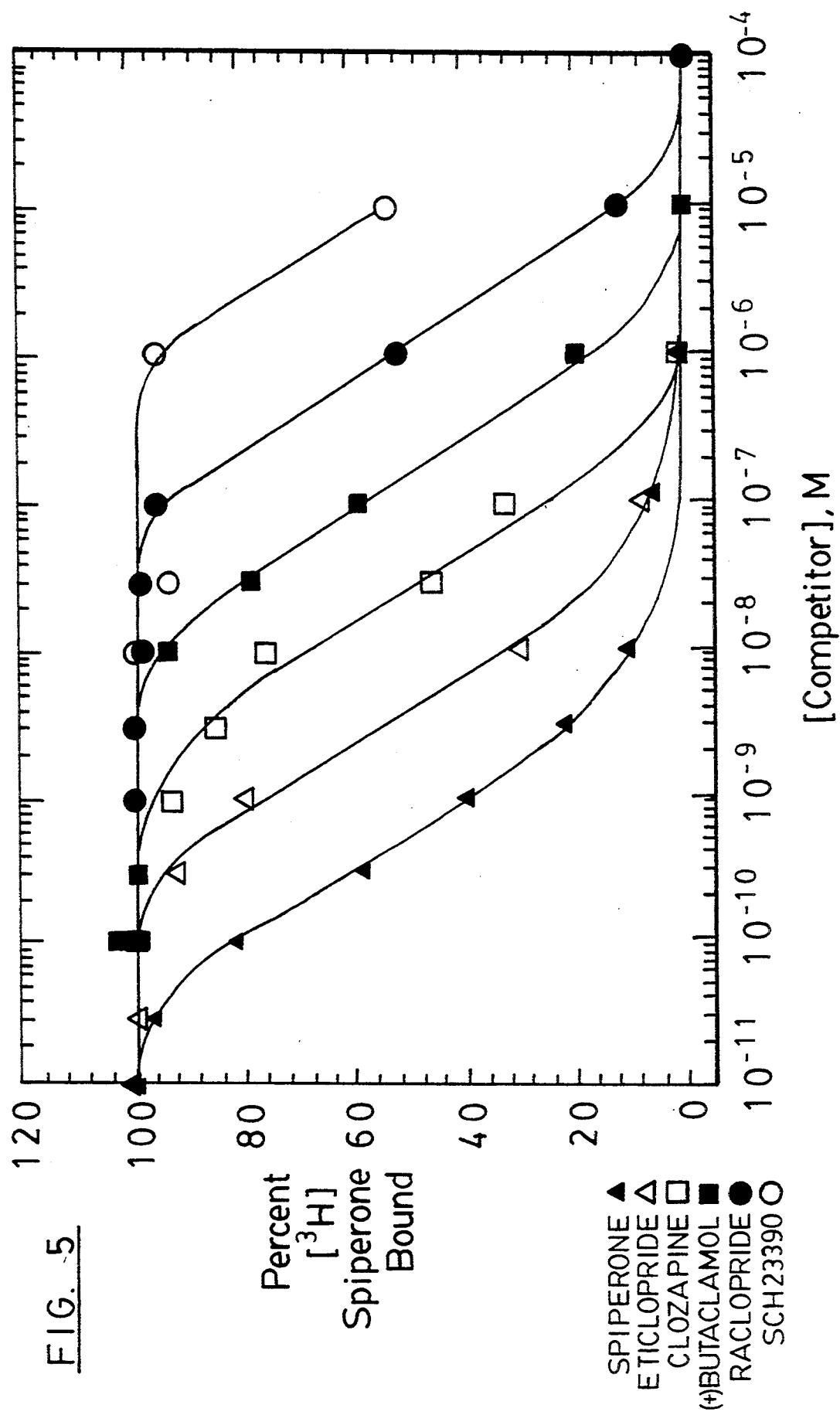

DNA SEQUENCE FOR THE HUMAN DOPAMINE RECEPTOR D₄ AND EXPRESSION THEREOF IN MAMMALIAN CELLS

This invention was made with government support under NIMH grant MH-45614 awarded by the National Institutes of Health. The government has certain rights in the invention.

BACKGROUND OF THE INVENTION

This invention was made with government support under NIMH grant MH-45614 awarded by the National Institutes of Health. The government has certain rights in the invention.

1. Field Of the Invention

The invention relates to dopamine receptors from mammalian species and the genes corresponding to such receptors. In particular, it relates to the human dopamine receptor $D_4$. Specifically, the invention relates to the isolation, cloning and sequencing of the human $D_4$ receptor gene. The invention also relates to the construction of eukaryotic expression vectors capable of expression of the human $D_4$ dopamine receptor in cultures of transformed eukaryotic cells and the synthesis of the human $D_4$ dopamine receptor in such cultures. The invention relates to the use of such cultures of transformed eukaryotic cells producing the human $D_4$ dopamine receptor for the characterization of antipsychotic drugs.

2. Information Disclosure

Dopamine is a neurotransmitter that participates in a variety of different functions mediated by the nervous system, including vision, movement, and behavior. See generally Cooper, J. et al., "The Biochemical Basis of Neuropharmacology," 161-195 (Oxford University Press, NY 3d Ed. 1978). The diverse physiological actions of dopamine are in turn mediated by its interaction with two of the basic types of G protein-coupled receptors: $D_1$ and $D_2$, which respectively stimulate and inhibit the enzyme adenylyl cyclase. Kebabian, J. and Calne, D., Nature 277:93-96 (1979). Alterations in the number or activity of these receptors may be a contributory factor in disease states such as Parkinson's disease (a movement disorder) and schizophrenia (a behavioral disorder).

A great deal of information has accumulated on the biochemistry of the $D_1$ and $D_2$ dopamine receptors, and methods have been developed to solubilize and purify these receptor proteins. See Senogles, S. et al., Biochemistry 25: 749-753 (1986); Sengoles, S. et al., J. Biol. Chem. 263: 18996-19002 (1988); Gingrich, J. et al., Biochemistry 27:3907-3912 (1988); Gingrich, J. et al. (in press). The $D_1$ dopamine receptor in several tissues appears to be a glycosylated membrane protein of about 72 kDa. Amlaiky, N. et al., Mol. Pharmacol. 31:129-134 (1987); Ninik, H. et al., Biochemistry 27:7594-7599 (1988). The $D_2$ receptor has been suggested to have a higher molecular weight of about 90-150 kDa. Amlaiky, N. and Caron, M., J. Biol. Chem. 260:1983-1986 (1985); Amlaiky, N. and Caron, M., J. Neurochem. 47:196-204 (1986); Jarvie, J. et al., Mol. Pharmacol. 34: 91-97 (1988). Much less is known about a recently discovered additional dopamine receptor, termed $D_3$. Sokoloff, P. et al., Nature 947:146-151 (1990). Dopamine receptors are primary targets in the clinical treatment of psychomotor disorders such as Parkinson's disease and affective disorders such as schizophrenia. Seeman, P. et al., Neuropsychopharm. 1:5-15 (1987); Seeman, P., Synapse 1:152-333 (1987). The three different dopamine receptors ($D_1$, $D_2$, $D_3$) have been cloned as a result of nucleotide sequence homology which exists between these receptor genes. Bunzow, J. R. et al., Nature 336:783-787 (1988); Grandy, D. K. et al., Proc. Natl. Acad. Sci. U.S.A. 86:9762-9766 (1989); Dal Toso, R. et al., EMBO J. 8: 4025-4034 (1989); Zhou, Q-Y. et al., Nature 346:76-80 (1990); Sunahara, R. K. et al., Nature 34(5:80-83 (1990); Sokoloff, P. et al., Nature 347:146-151 (1990).

The antipsychotic clozapine is useful for socially withdrawn and treatment-resistant schizophrenics [Kane, J. et al., Nature 947:146-151 (1990)], but unlike other antipsychotic drugs, clozapine does not cause tardive dyskinesia [Casey, D. E., Psychopharmacology 99: 547-553 (1989)]. Clozapine, however, has dissociation constants at $D_2$ and $D_3$ which are 3 to 30-fold higher than the therapeutic free concentration of clozapine in plasma water [Ackenheil, M. et al., Arzneim-Forsch 2(5:1156-1158 (1976); Sandoz Canada, Inc., Clozaril: Summary of preclinical and clinical data (1990)]. This suggests the existence of dopamine receptors more sensitive to the antipsychotic clozapine.

We have cloned and sequenced such a human dopamine receptor which we term $D_4$. The dopamine $D_4$ receptor gene has high homology to the human dopamine $D_2$ and $D_3$ receptor genes. The pharmacological profile of this receptor resembles that of the $D_2$ and $D_3$ receptors but it has an affinity for clozapine which is tenfold higher. The present inventors envision that the D4 dopamine receptor disclosed as this invention may prove useful in discovering new types of drugs for schizophrenia that like clozapine do not induce tardive dyskinesia and other motor side effects.

SUMMARY OF THE INVENTION

The present invention is directed toward the isolation, characterization and pharmacological use of the human $D_4$ dopamine receptor, the gene corresponding to this receptor, a recombinant eukaryotic expression vector capable of expressing the human $D_4$ dopamine receptor in cultures of transformed eukaryotic cells and such cultures of transformed eukaryotic cells that synthesize the human $D_4$ dopamine receptor.

It is an object of the invention to provide a nucleotide sequence encoding a mammalian dopamine receptor. Further, it is an object of the invention to provide a nucleotide sequence that encodes a mammalian dopamine receptor with novel and distinct pharmacological properties. It is specifically an object of the invention to provide a nucleotide sequence encoding a mammalian dopamine receptor having the particular drug dissociation properties of the human dopamine receptor $D_4$. In particular, the mammalian dopamine receptor encoded by the nucleotide sequence of the present invention has a high affinity for the drug clozapine. The human $D_4$dopamine receptor embodied in the present invention shows a biochemical inhibition constant (termed $K_i$) of 1-40 nanomolar (nM), preferably 1-20 nM, most preferably 11 nM clozapine, as detected by the [³H]spiperone binding assay disclosed herein. The human $D_4$ dopamine receptor embodied in the present invention displays the following pharmacological profile of inhibition of [³H]spiperone binding in the [³H]spiperone binding assay: spiperone > eticlopride > clozapine > (+)-butaclamol > ratiopride > SCH23390. In a preferred embodiment of the invention, the nucleotide sequence encoding a dopamine receptor encodes the human dopamine receptor $D_4$.

The present invention includes a nucleotide sequence encoding a mammalian dopamine receptor derived from a cDNA molecule isolated from a cDNA library constructed with RNA from the human neuroblastoma cell line SK-N-MC. In this embodiment of the invention, the nucleotide sequence includes 780 nucleotides of the human $D_4$ dopamine receptor gene comprising transmembrane domains V, VI and VII and 126 nucleotides of 3' untranslated sequence (SEQ ID Nos.: 8,12 and 15).

The invention also includes a nucleotide sequence derived from human genomic DNA (SEQ ID Nos.: 1,3-5, 7, 8, 10-12, 14 and 15). In this embodiment of the invention, the nucleotide sequence includes 5 kilobases (kb) of human genomic DNA encoding the dopamine receptor $D_4$. This embodiment includes the sequences present in the cDNA embodiment, an additional 516 nucleotides of coding sequence comprising transmembrane domains I, II, III, and IV, and 590 nucleotides of 5' untranslated sequence. This embodiment of the invention also contains the sequences of four intervening sequences that interrupt the coding sequence of the human $D_4$ dopamine receptor gene.

The invention includes a nucleotide sequence of a human $D_4$ receptor molecule, and includes allelic variations of this nucleotide sequence and the corresponding $D_4$ receptor molecule, either naturally occurring or the product of in vitro chemical or genetic modification, having essentially the same nucleotide sequence as the nucleotide sequence of the human $D_4$ receptor disclosed herein, wherein the resulting human $D_4$ receptor molecule has substantially the same drag dissociation properties of the human $D_4$ receptor molecule corresponding to the nucleotide sequence described herein.

The invention also includes a predicted amino acid sequence for the human $D_4$ dopamine receptor deduced from the nucleotide sequence comprising the complete coding sequence of the $D_4$ dopamine receptor gene (SEQ ID Nos.: 2, 6, 9, 13 and 16 and SEQ ID No.:17).

This invention provides both nucleotide and amino acid probes derived from these sequences. The invention includes probes isolated from either the cDNA or genomic DNA clones, as well as probes made synthetically with the sequence information derived therefrom. The invention specifically includes but is not limited to oligonucleotide, nick-translated, random primed, or in vitro amplified probes made using the cDNA or genomic clone embodying the invention, and oligonucleotide and other synthetic probes synthesized chemically using the nucleotide sequence information of the cDNA or genomic clone embodiments of the invention.

It is a further object of this invention to provide sequences of the human $D_4$ dopamine receptor for use as a probe to determine the pattern, amount and extent of expression of this receptor in various tissues of mammals, including humans. It is also an object of the present invention to provide probes derived from the sequences of the human $D_4$ dopamine receptor to be used for the detection and diagnosis of genetic diseases. It is an object of this invention to provide probes derived from the sequences of the human $D_4$ dopamine receptor to be used for the detection of novel related receptor genes.

The present invention also includes synthetic peptides made using the nucleotide sequence information comprising the cDNA or genomic clone embodiments of the invention. The invention includes either naturally occurring or synthetic peptides which may be used as antigens for the production of $D_4$ dopamine receptor-specific antibodies, or used for competitors of the $D_4$ receptor molecule for drug binding, or to be used for the production of inhibitors of the binding of dopamine or dopamine analogs of the $D_4$ dopamine receptor molecule.

In addition, this invention includes a cloning vector comprising the human $D_4$ dopamine receptor and sequences that mediate the replication and selected growth of microorganisms that carry this vector.

The present invention provides a recombinant expression vector comprising the nucleotide sequence of the human $D_4$ dopamine receptor and sequences sufficient to direct the synthesis of human $D_4$ dopamine receptor in cultures of transformed eukaryotic cells. In a preferred embodiment, the recombinant expression vector is comprised of plasmid sequences derived from the plasmid pCD-PS and a hybrid human $D_4$ dopamine gene. This hybrid human $D_4$ dopamine gene is comprised of the entirety of the genomic sequences from a particular $D_4$ dopamine genomic clone described herein, up to a PstI site located in exon III, followed by the remainder of the coding and 3' untranslated sequences found in a particular human cDNA sequence derived from a human neuroblastoma cell line. This invention includes a recombinant expression vector comprising essentially the nucleotide sequences of genomic and cDNA clones of the human $D_4$ dopamine receptor in an embodiment that provides for their expression in cultures of transformed eukaryotic cells.

It is also an object of this invention to provide cultures of transformed eukayotic cells that have been transformed with such a recombinant expression vector and that synthesize human $D_4$ dopamine receptor protein. In a preferred embodiment, the invention provides monkey COS cells that synthesize human $D_4$ dopamine receptor protein.

The present invention also includes protein preparations of the human $D_4$ dopamine receptor, and preparations of membranes containing the human $D_4$ dopamine receptor, derived from cultures of transformed eukaryotic cells. In a preferred embodiment, cell membranes containing human $D_4$ dopamine receptor protein is isolated from culture of COS-7 cells transformed with a recombinant expression vector that directs the synthesis of human $D_4$ dopamine receptor.

It also an object of this invention to provide the human $D_4$ dopamine receptor for use in the in vitro screening of novel antipsychotic compounds. In a preferred embodiment, membrane preparations containing the human $D_4$ dopamine receptor, derived from cultures of transformed eukaryotic cells, are used to determine the drug dissociation properties of antipsychotic compounds in vitro. These properties are then used to characterize novel antipsychotic compounds by comparison to the binding properties of known antipsychotic compounds.

The present invention will also be useful for the in vivo detection of dopamine and a dopamine analog, known or unknown, either naturally occurring or as the embodiments of antipsychotic or other drugs.

It is an object of the present invention to provide a method for the quantitative detection of dopamine and a dopamine analog, either naturally occurring or as the embodiments of antipsychotic or other drugs. It is an additional object of the invention to provide a method to detect dopamine or a dopamine analog in blood, saliva, semen, cerebrospinal fluid, plasma, lymph, or any other bodily fluid.

Restriction map of the genomic human dopamine $D_4$ receptor clone and alignment with the genomic intron-/exon organization of the human dopamine $D_2$ receptor. Relevant restriction endonuclease sites in the $D_4$ receptor are indicated. The SalI site is part of the cloning site in EMBL3. The proposed coding regions are boxed and numbered in Roman numerals. Perfect matches of proposed intron/exon junction sites are indicated by connecting stippled bars between the receptor clones.

FIG. 2. The nucleotide sequence of genomic and cDNA clones of human $D_4$ dopamine receptor gene (SEQ ID Nos.: 1, 3–5, 7, 8, 10–12, 14 and 15).

Nucleotide and deduced amino acid sequence of the human dopamine receptor gene and cDNA. The putative coding sequence is in capitals (non-coding sequence is in italics) and deduced amino acid sequence is shown above the nucleotide sequence. Numbering of the putative coding sequence begins with the first methionine of the open reading frame. The sequence corresponding to the cDNA clone is hatched.

Figure 3C:
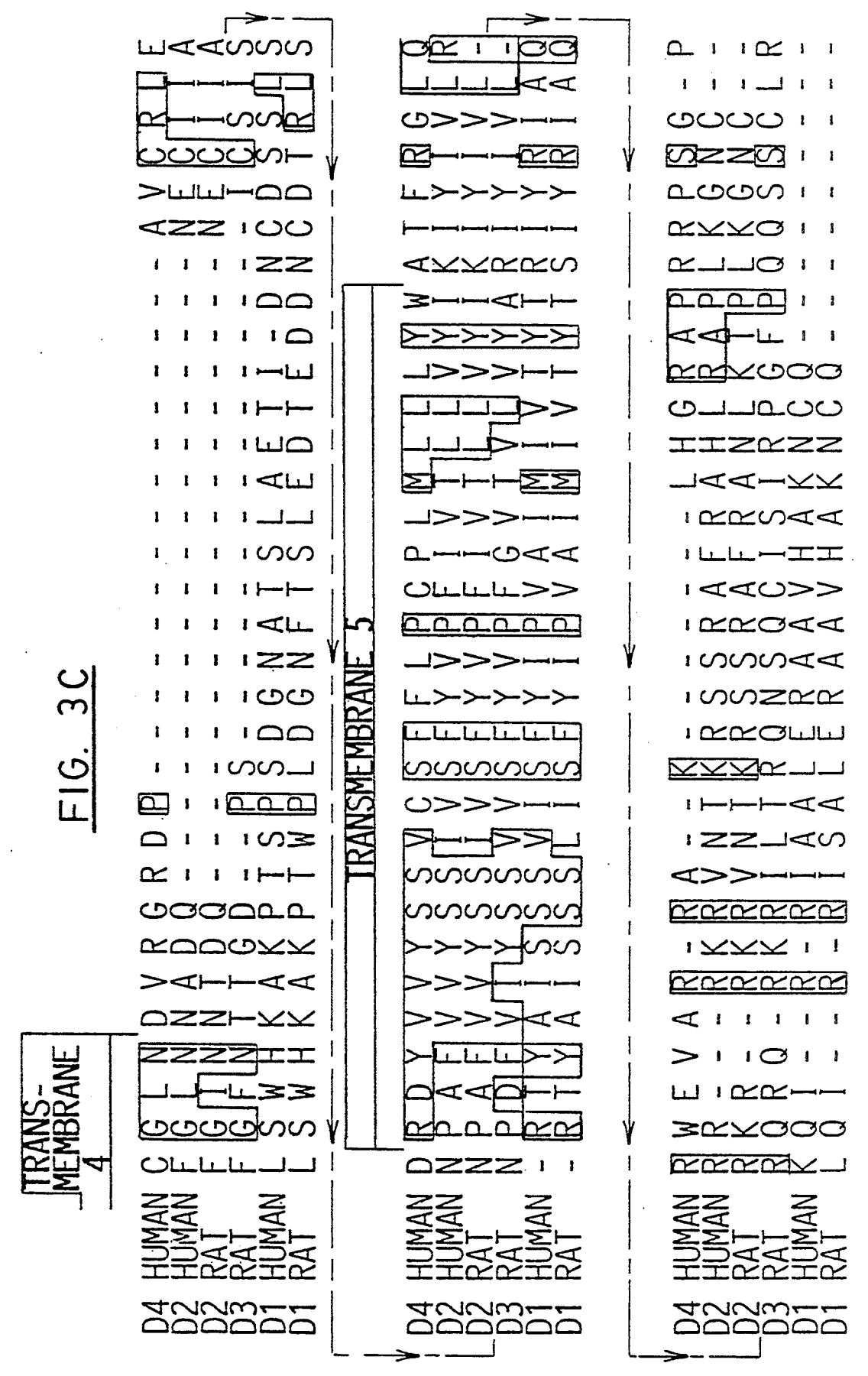
Figure 3D:
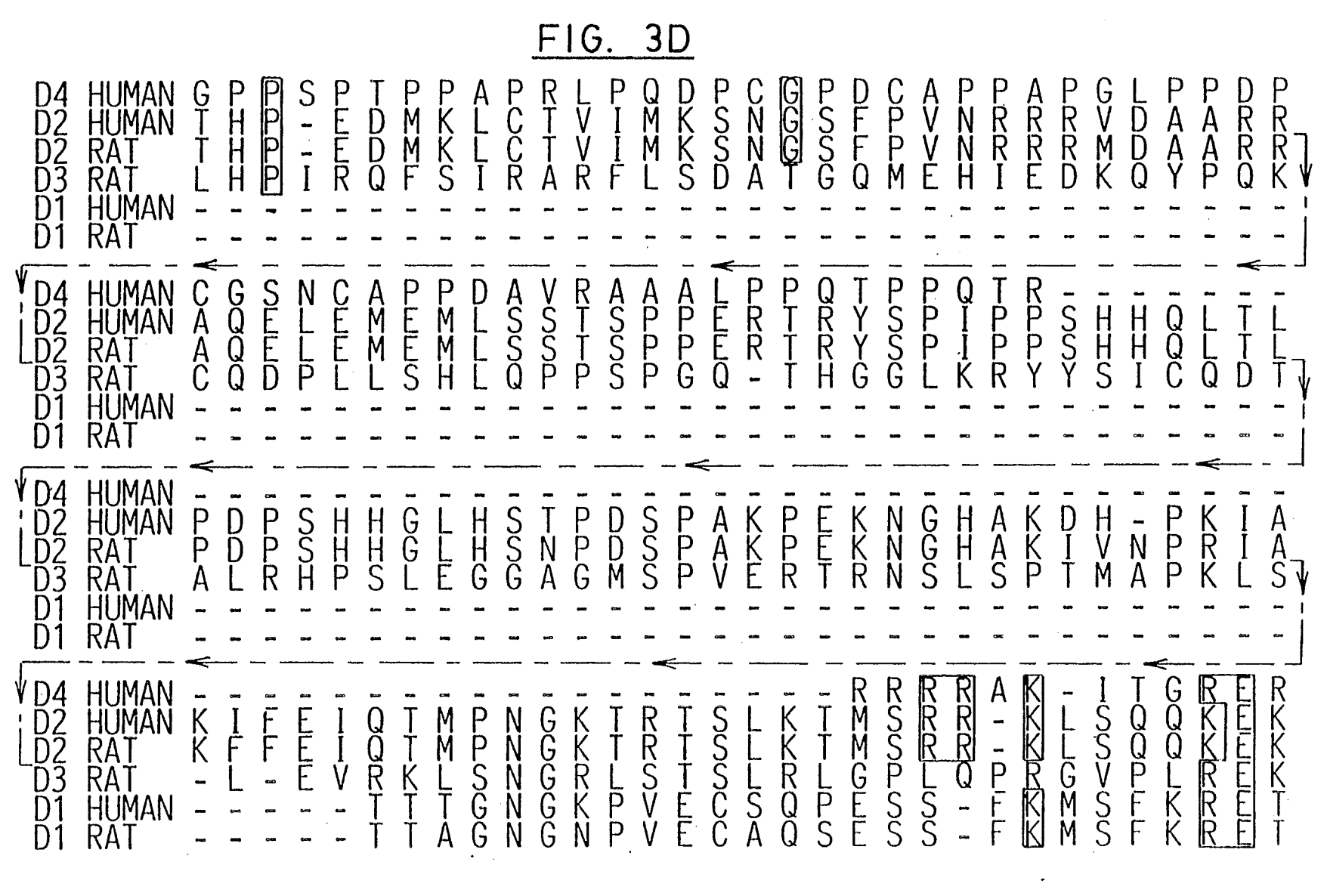

FIGS. 3A through 3F. Amino acid sequence alignment of mammalian dopamine receptors Alignment of the putative amino acid sequence of the human (SEQ ID No.:19) and rat (SEQ ID No.:18) $D_2$, rat $D_3$ (SEQ ID No.:20) and human (SEQ ID No.:21) and rat (SEQ ID No.:22) $D_1$ receptor. Amino acids conserved within the group of dopamine receptors are shaded. The putative transmembrane domains are overlined and labeled by Roman numerals.

Figure 4:
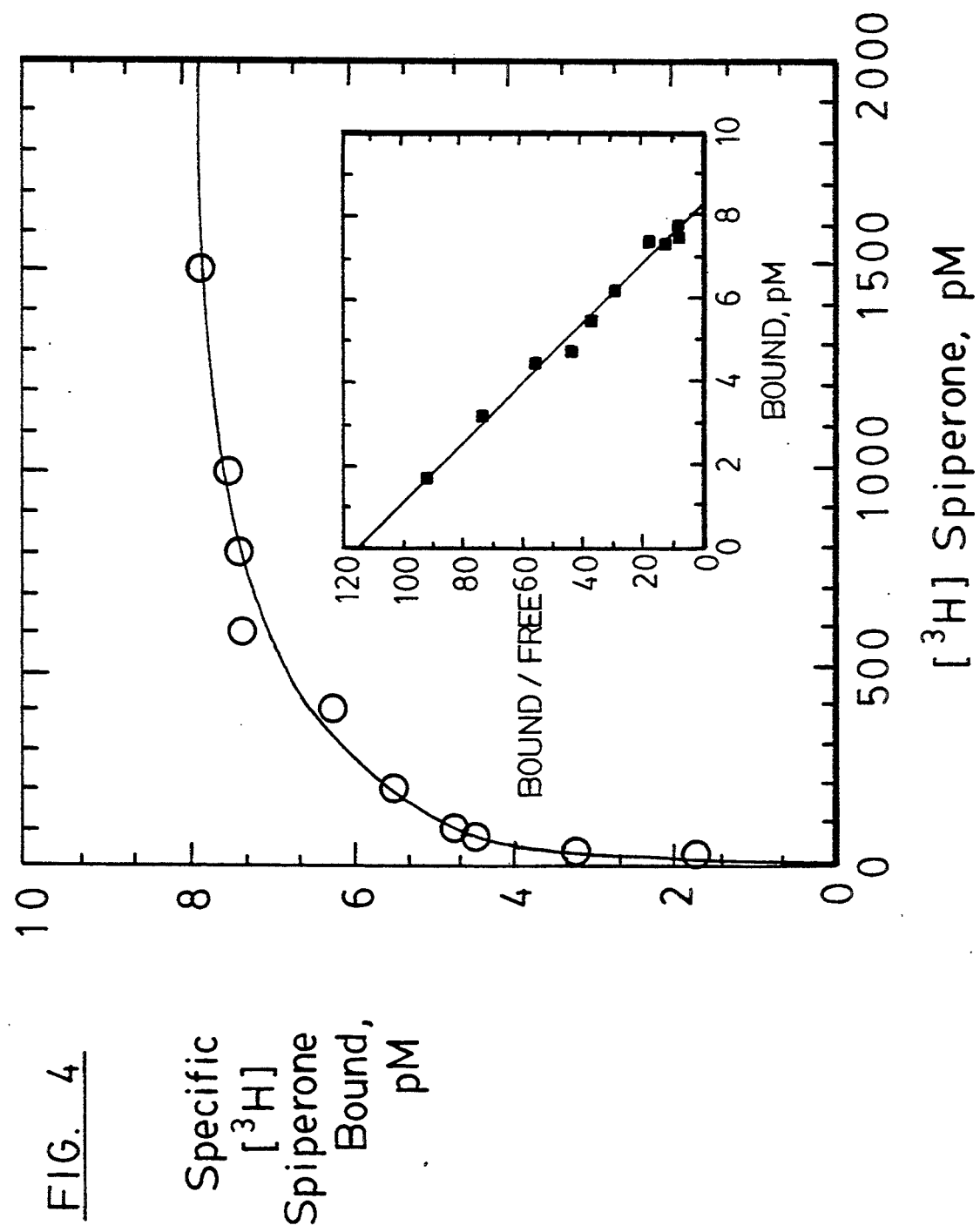

FIG. 4. Binding of [$^3$H]spiperone to transfected COS-7 cell membranes.

Saturation isotherms of the specific binding of [$^3$H]spiperone to membranes from COS-7 cells expressing the cloned human dopamine $D_4$ receptor. The results shown are representative of two independent experiments each conducted in duplicate. Inset, Scatchard plot of the same data. Estimated $B_{max}$ (approximately 260 fmol/mg protein) and $K_i$ (70 pM) values were obtained by LIGAND computer program.

FIG. 5. Pharmacological specificity of [$^3$H]spiperone binding to transfected COS-7 cells.

Representative curves are shown for the concentration dependent inhibition of [$^3$H]spiperone binding by various dopaminergic agonist and antagonists. Data were analyzed by LIGAND and the results shown are the means of duplicate determinations. Estimated $K_i$ values are listed in Table I along with the $K_i$ values obtained on the human $D_2$ receptor expressed in GH$_4$ZR7 cells.

DETAILED DESCRIPTION OF THE PREFERRED EMBODIMENTS

The term "$D_4$-dopamine receptor" as used herein refers to proteins substantially homologous to, and having substantially the same biological activity as, the protein coded for by the nucleotide sequence depicted in FIG. 2 (i.e., proteins which display high affinity binding to clozapine). This definition is intended to encompass natural allelic variations in the $D_4$ dopamine receptor sequence. Cloned genes of the present invention may code for $D_4$-dopamine receptors of any species of origin, including, mouse, rat, rabbit, cat, and human, but preferably code for receptors of mammalian, most preferably human, origin.

Nucleotide bases are abbreviated herein as follows:

| A = Adenine | G = Guanine |
|---|---|
| C = Cytosine | T = Thymine |

Amino acid residues are abbreviated herein to either three letters or a single letter as follows:

| Ala;A = Alanine | Leu;L = Leucine |
|---|---|
| Arg;R = Arginine | Lys;K = Lysine |
| Asn;N = Asparagine | Met;M = Methionine |
| Asp;D = Aspartic acid | Phe;F = Phenylalanine |
| Cys;C = Cysteine | Pro;P = Proline |
| Gln;Q = Glutamine | Ser;S = Serine |
| Glu;E = Glutamic acid | Thr;T = Threonine |
| Gly;G = Glycine | Trp;W = Tryptophan |
| His;H = Histidine | Tyr;Y = Tyrosine |
| Ile;I = Isoleucine | Val;V = Valine |

The production of proteins such as the $D_4$-dopamine receptor from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the $D_4$-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the $D_4$-dopamine receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, $D_4$-dopamine receptor gene sequences may be obtained by use of the polymerase chain reaction (PCR) procedure, with the PCR oligonucleotide primers being produced from the $D_4$-dopamine receptor gene sequence provided herein. See U.S. Pat. Nos. 4,683,195 to Mullis et al. and 4,683,202 to Mullis.

The $D_4$-dopamine receptor may be synthesized in host cells transformed with vectors containing DNA encoding the $D_4$-dopamine receptor. A vector is a replicable DNA construct. Vectors are used herein either to amplify DNA encoding the $D_4$-dopamine receptor and/or to express DNA which encodes the $D_4$-dopamine receptor. An expression vector is a replicable DNA construct in which a DNA sequence encoding the $D_4$ receptor is operably linked to suitable control sequences capable of effecting the expression of the $D_4$ receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the $D_4$ receptor vectors constructed using recombinant DNA techniques. Transformed host cells ordinarily express the $D_4$ receptor, but host cells transformed for purposes of cloning or amplifying the $D_4$ receptor DNA need not express the $D_4$ receptor. When expressed, the $D_4$ receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant $D_4$-dopamine receptor synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters of SV40 are useful because both are obtained easily from the virus as a fragment which also contains the SV40 viral origin of replication. See Fiers et al., Nature 273:113 (1978). Further, the human genomic $D_4$ receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g., Polyoma, Adenovirus, VSV, or MPV), or may be provided by the host cell chromosomal replication mechanism. If the vector is integrated into the host cell chromosome, the latter may be sufficient.

$D_4$-dopamine receptors made from cloned genes in accordance with the present invention may be used for screening compounds for $D_4$ dopamine receptor activity, or for determining the amount of a dopaminergic drug in a solution (e.g., blood plasma or serum). For example, host cells may be transformed with a vector of the present invention, $D_4$-dopamine receptors expressed in that host, the cells lysed, and the membranes from those cells used to screen compounds for $D_4$-dopamine receptor binding activity. Competitive binding assays in which such procedures may be carded out are well known, as illustrated by the Examples below. By selection of host cells which do not ordinarily express a dopamine receptor, pure preparations of membranes containing $D_4$ receptors can be obtained. Further, $D_4$-dopamine receptor agonist and antagonists can be identified by transforming host cells with vectors of the present invention. Membranes obtained from such cells can be used in binding studies wherein the drug dissociation activity is monitored. Such cells must contain $D_4$ protein in the plasma and other cell membranes. Procedures for carrying out assays such as these are also described in greater detail in the Examples which follow.

Cloned genes and vectors of the present invention are useful in molecular biology to transform cells which do not ordinarily express the $D_4$dopamine receptor to thereafter express this receptor. Such cells are useful as intermediates for making cell membrane preparations useful for receptor binding assays, which are in turn useful for drug screening. Further, genes and vectors of the present invention are useful in gene therapy. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carded out homologous recombination or site-directed mutagenesis. See generally Thomas, K. and Capecchi, M., Cell 51: 503–512 (1987); Bertling, W., Bioscience Reports 7:107–112 (1987); Smithies, O. et al., Nature 317;230–234 (1985).

Cloned genes of the present invention, and oligonucleotides derived therefrom, are useful for screening for restfiction fragment length polymorphism (RFLP) associated with certain genetic disorders.

Oligonucleotides of the present invention are useful as diagnostic tools for probing $D_4$-receptor gene expression in nervous tissue. For example, tissue can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of a $D_4$-dopamine receptor gene, and potential pathological conditions related thereto, as also illustrated by the Examples below.

The Examples which follow are illustrative of specific embodiments of the invention, and various-uses thereof. They are set forth for explanatory purposes only, and are not to be taken as limiting the invention.

EXAMPLE 1

Screening Tissue and Cell Line RNA for Donamine-Like Receptor Expression

RNA was prepared from different rat tissues or cell lines using the guadinium thiocyanate/CsCl procedure described in Bunzow et al., Nature 336:783-787 (1988). The tissues included heart, epididymis, testis, gut, pancreas, spleen, thymus, muscle, ventricle, atria, lung, adrenal, kidney, liver, pineal gland and pituitary. The cell lines screened included SK-N-MC, SK-N-SH, COS, AKR1, Ltk−, GH4C1, NG108-15, ART20, 3T3, BSC40, C6, CV-1, Hela, IMR-32, N4TG1, NCB-20, PC-12, Rion m5f and WERI-Rb-1. 20 μg of RNA was analyzed by Northern blot hybridization with a radiolabeled BstYI-BglII DNA fragment of the rat $D_2$ receptor, which encodes the putative transmembrane domains VI and VII. The hybridization conditions used were 25% formamide, 1M NaCl, 1% SDS, 100 μg/ml denatured salmon sperm DNA, 0.2% polyvinylpirolidone, 0.2% Ficoll, and 0.05M Tris/HCl (pH 7.4); hybridization was performed overnight at 37° C. The blot was then washed at 55° C. in 2× standard saline-citrate (SSC) and 1% sodium dodecyl sulfate (SDS). Exposure was for two days at −70° C. using an intensifying screen. For comparison, the same blot was hybridized under high stringency conditions, which are the same conditions using 50% formamide and 42° C. for the hybridication and 0.2× SSC for the wash. Under high and low stringency only the adrenal gland showed a positive signal while under low stringency the SK-N-MC line also showed a signal.

EXAMPLE 2

Construction of a cDNA Phage Library using Neuroblastoma RNA

Double-stranded cDNA was synthesized using standard techniques [see Sambrook, J. et al., *Molecular Cloning: A Laboratory Manual*, 2d ed., Cold Spring Harbor Laboratory Press 1989] from poly(A)+mRNA isolated from the human neuroblastoma cell line SK-N-MC as described in Example 1. The cDNA was directionally cloned into the EcoRI and XhoI restriction endonuclease sites of the phage cloning vector lambda ZAPII (Stratagene, 11099 North Torrey Pines Road, La Jolla, Cal. 92037). The library was transferred to colony plaque screen filters (New England Nuclear, 549 Albany Street, Boston, Mass. 02118) and prehybridized overnight at 37° C. in 25% formamide, 0.2% polyvinylpyrolidone, 0.2% Ficoll, 0.05M Tris/HCl (pH 7.5), 1M NaCl, 0.1% pyrophosphate, 1% SDS and denatured salmon sperm DNA (100/μg/ml). Approximately 500,000 independent clones were screened under low-stringency conditions of hybridization. Hybridization was performed for 30 hrs with 1.6 kb BamHI - BglII and 300 bp BstYI - BglII fragments of a rat $D_2$ receptor clone, $^{32}$P-labeled using a random primed labeling system (Boehringer Mannheim Biochemicals, P.O. Box 50414, Indianapolis, Ind. 46250) at a specific activity of $10^6$ dpm/μg. Filters were washed at 55° C. in 2× SSC and 1% SDS. The clone $D_2$10S was isolated and sequenced using the Sanger dideoxy chain termination method catalyzed by Sequenase (U.S. Biochemical Corporation, P.O. Box 22400, Cleveland, Ohio 44122). The sequence of this clone is shown in FIG. 2 (hatched area) (SEQ ID NOS.: 8, 12 and 15).

EXAMPLE 3

Screening a Genomic DNA Phage Library with a Human Dopamine Receptor Probe

Figure 1:
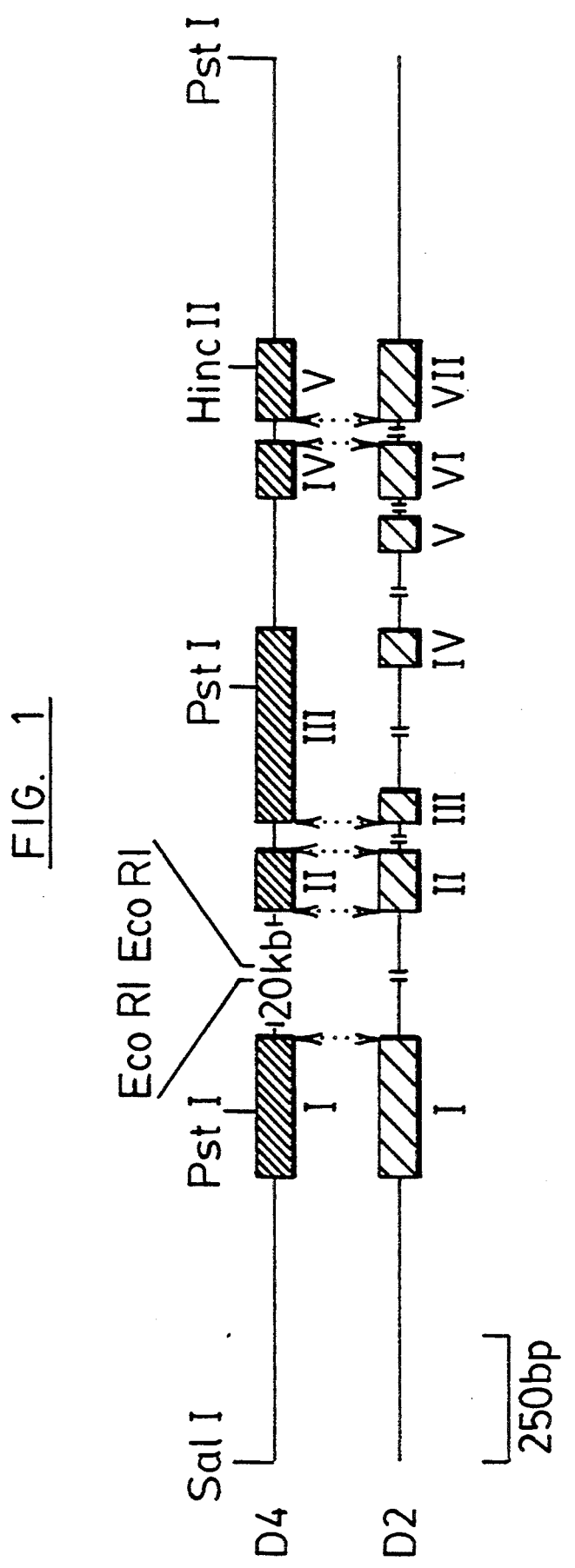
FIG. 1. The structure of a genomic clone comprising the human $D_4$ dopamine receptor gene.
Figure 3A:
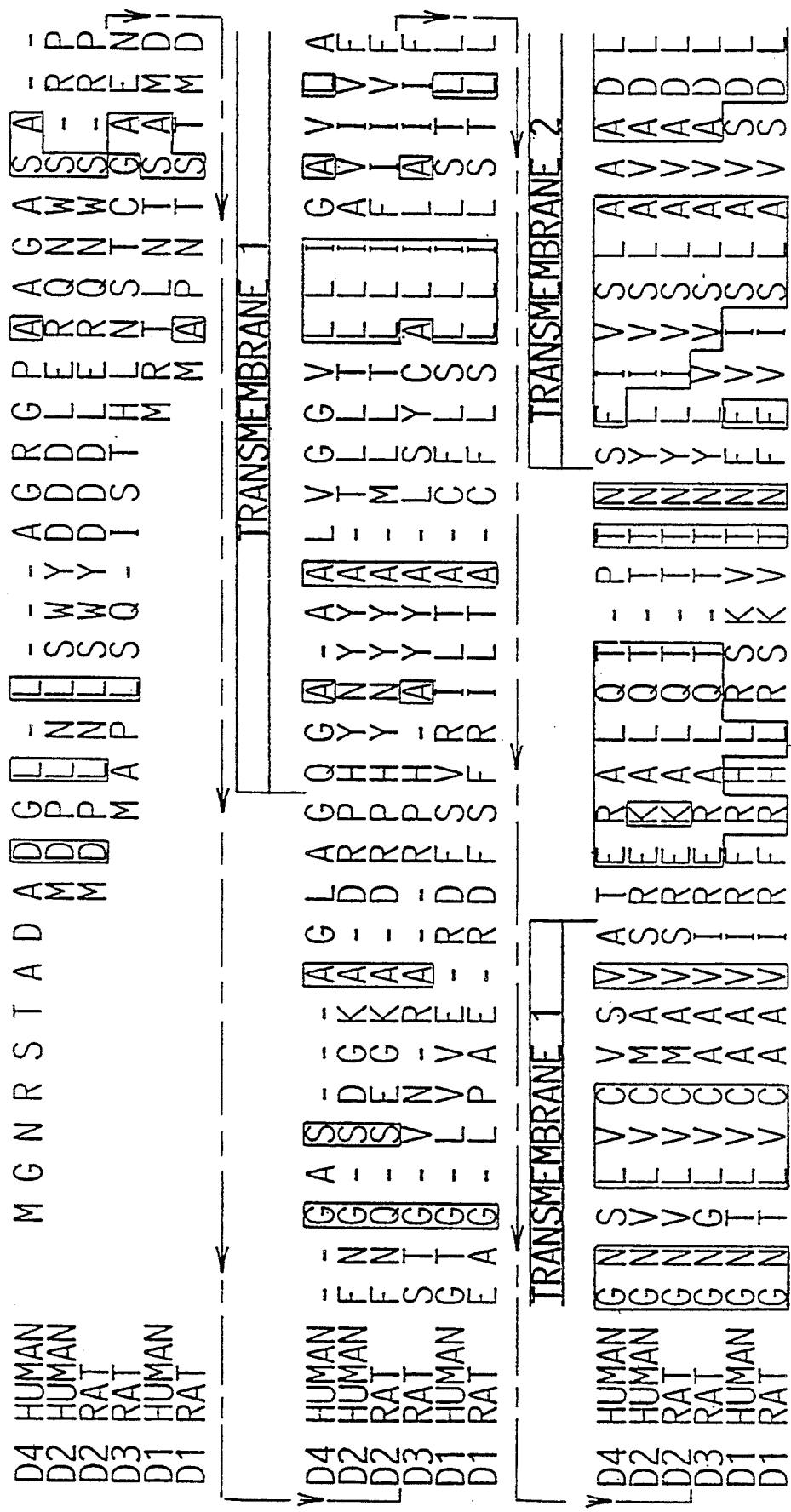
Figure 3B:
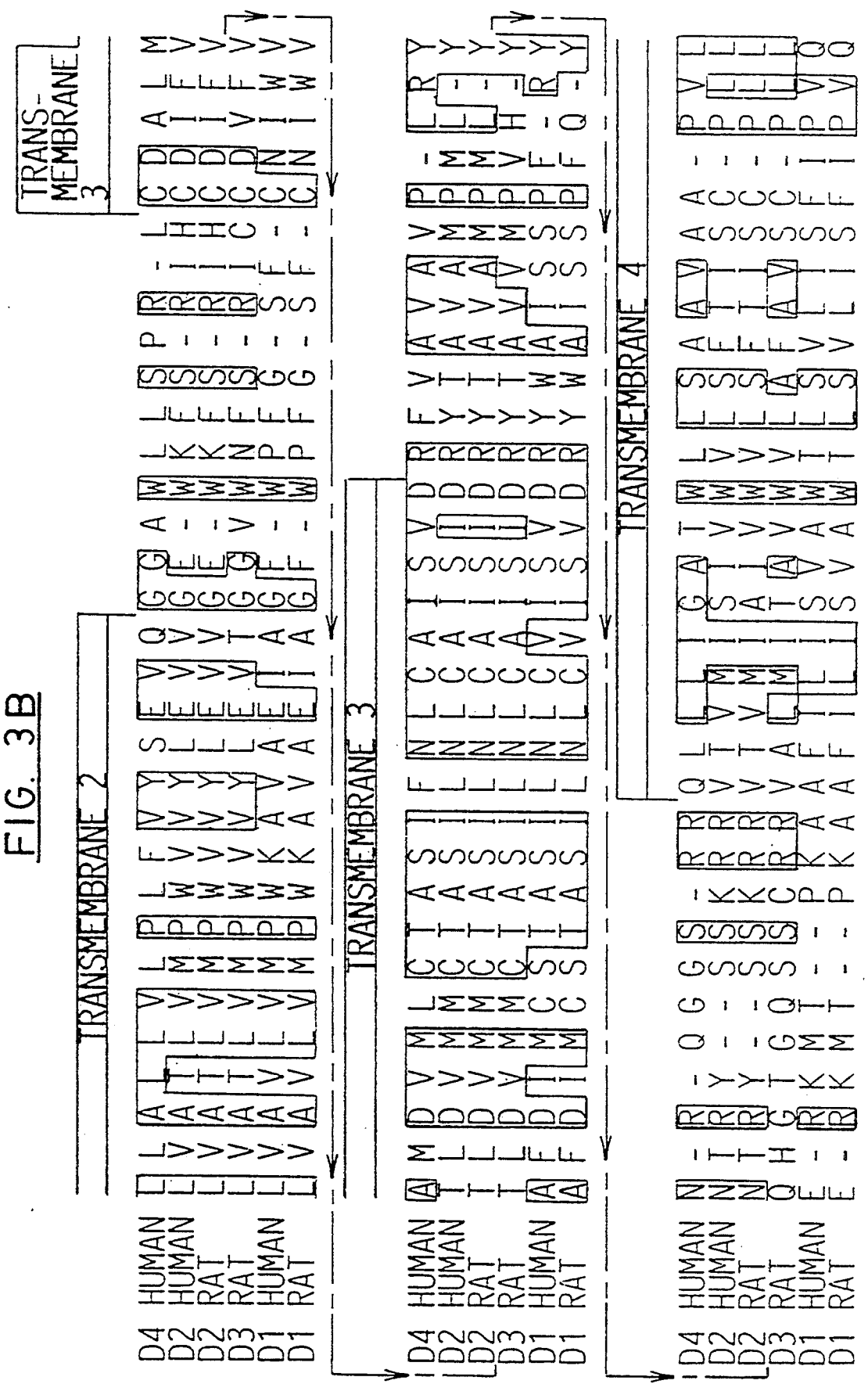
Figure 3E:
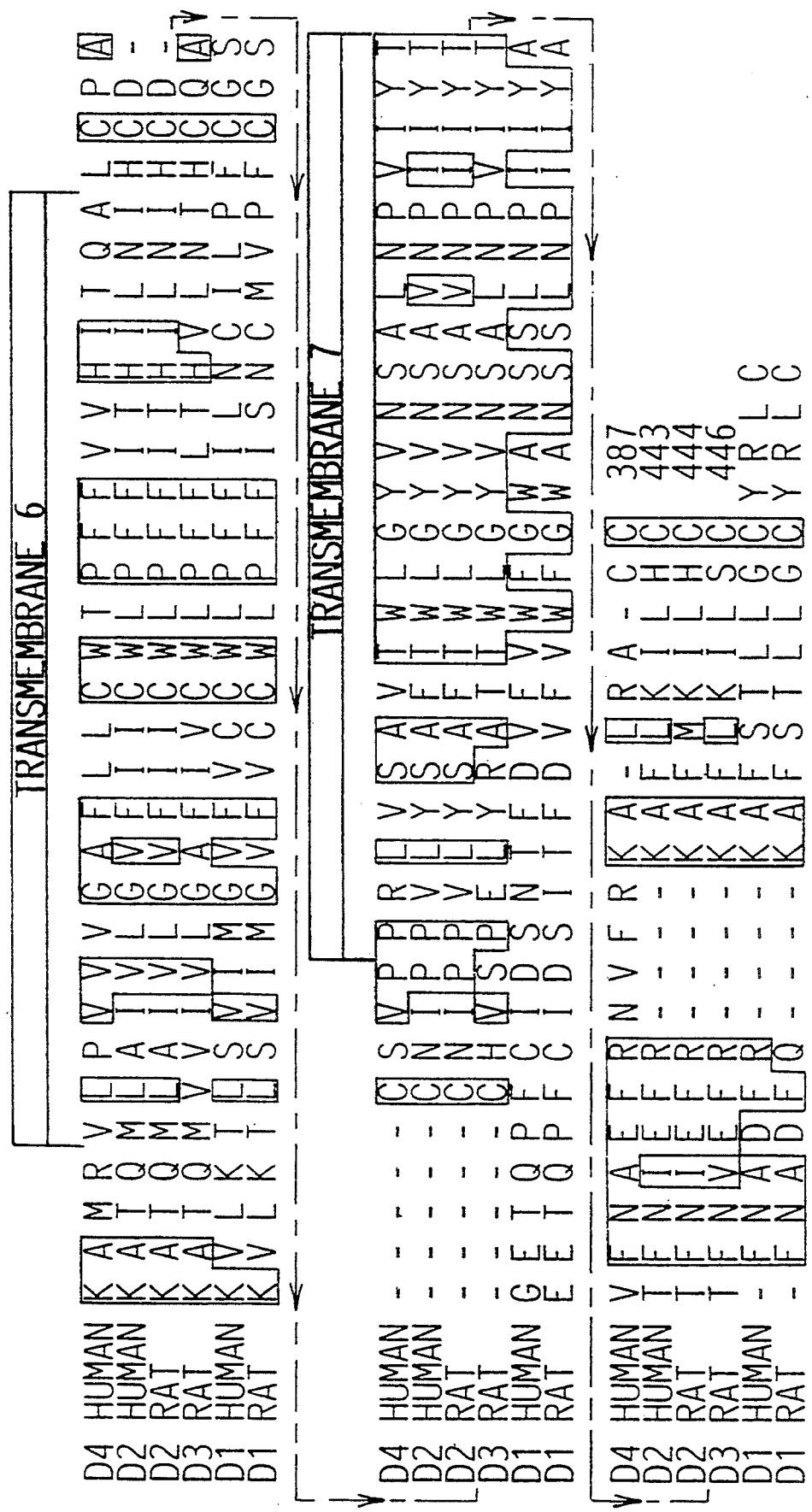

Clone $D_2$10S was 32P-labeled by random primed synthesis and used to screen a commercially available human genomic library cloned in the phage vector EMBL3 (Clonetech). Hybridization was performed as described in Example 2 using with 50% formamide. After hybridization the filters were washed at 65° C. in 0.1× SSC and 0.1% SDS. The clone $D_2$10G was isolated and analyzed by restriction endonuclease and Southern blot analysis. The map of this genomic clone is shown in FIG. 1, wherein the structure of the $D_4$ receptor gene is compared with the structure of the $D_2$ gene. 1.3 kb and 2.6 kb PstI - PstI fragments and an overlapping 2.0 kb SalI- EcoRI fragment of the $D_4$ receptor gene were subcloned into the plasmid pBluescript-SK (Stratagene). The subcloned fragments were characterized by sequence analysis as described above. This sequence is shown in FIG. 2 (SEQ ID NOS.: 1, 3–5, 7, 8, 10–12, 14 and 15).

EXAMPLE 4

DNA Sequence Analysis of the Human $D_4$ Dopamine Receptor

One of the cDNA clones detected by screening the SK-N-MC neuroblastoma library with a rat $D_2$ probe at low stringency ($D_2$10S) contained a 780 bp EcoRI-XhoI insert which hybridized to the rat probe. Sequence analysis of this insert showed the presence of an open reading frame with homology to the amino acid sequence of transmembrane domains V (45%), VI (46%) and VII (78%) of the $D_2$ receptor as shown in FIGS. 3A through 3F.

Screening of a human genomic EMBL3 library (Clontech) under high stringency conditions with the clone $D_2$10S resulted in the isolation of the genomic clone $D_2$10G. Southern blot and sequence analysis indicated that the clone contained a 5 kb SalI-PstI fragment which coded for the entire gene of $D_2$10S. Sequence analysis revealed, 590 bp downstream from the SalI site, a potential translation initiation codon (ATG) followed by an open reading frame that showed amino acid sequence homolog), with transmembrane domain I (36%) and II (63%) of the $D_2$ receptor. Almost immediately downstream from transmembrane domain II, hornology to the $D_2$ receptor disappears, indicating the presence of an intron in the genomic DNA. This intron spanned approximately 2 kb, after which sequence homolog), to the $D_2$ receptor was re-established. Translation of the putative gene product shown homology to the transmembrane domains III (68%), IV (37%), V(46%) and VII (78%) of the $D_2$ receptor (see FIGS. 3A through 3F).

Potential splice junction donor and acceptor sites (Mount, *Nucl. Acids Res.* 10:461–472, 1982) were found in the transmembrane domains II, III and VI, as shown in FIG. 1. These splice sites were at an identical position as in the $D_2$ and $D_3$ receptor gene [see Grandy, D. K. et al., Proc. Natl. Acad. Sci. U.S.A. 86:9762–9766 (1989); Dal Toso, R. et al., EMBO J. 8: 4025–4034 (1989); Sokoloff, P. et al., Nature 347:146-151 (1990)] and FIG. 1. The coding sequence downstream from transmembrane domain IV is identical to the sequence of clone $D_2$10S but is interrupted by an intron of about 300 bp between transmembrane domain V and VI and an additional intron of 92 bp in transmembrane VI (FIG. 1, hatched area). The precise location of the splice site for the intron between transmembrane V and VI cannot be determined due to the fact that a sequence of 52 bp present in the coding sequence is repeated exactly on either side of the intron (FIG. 2).

The deduced amino acid sequence from the genomic and cDNA nucleotide sequences indicated that this gene codes for a protein of 387 amino acids with an apparent molecular weight of 41 kD (SEQ ID NOS.: 2, 6, 9, 13 and 16 and SEQ ID NO.: 17). A hydrophobicity plot of the protein sequence suggests the existence of seven transmembrane domains. These regions correlate with the observed homologous regions in the human $D_2$ receptor and other receptors belonging to the family of G-protein coupled receptors [Bunzow, J. R. et al., *Nature* 336:783-787 (1988); Sokoloff, P. et al., *Nature* 3.47:146-151 (1990); Dohlman, H. G. et al., *Biochemistry* 26: 2657-2664 (1987) and FIG. 2]. Two amino acids downstream from the initiation methionine is a potential N-linked glycosylation site [Hubbard, S. & Ivatt, R., *Annu. Rev. Biochem.* 50:, 555-583 (1981)]. The amino acid residues Asp (80) and Asp (115) in the $D_4$ receptor, which are conserved within the family catecholaminergic receptors, are postulated to act as centurions in catecholamine binding [Strader, C. D. et al., *J. Biol. Chem.* 263: 10267-10271 (1988)]. Also conserved within the family of catecholaminergic receptors are Ser (197) and Ser (700) which have been suggested to interact with the catechol hydroxyl groups [Kozak, M., *Nucleic Acids Res.* 12: 857-872 (1984)]. Several consensus sites for potential phosphorylation by protein kinase C and protein kinase A are noted in the 3rd cytoplasmic loop [Sibley, D. R. et al., *Cell* 48:913-922 (1987); Bouvier, M. et al., *Nature* 333: 370-373 (1988)]. The Cys (187), which may serve as a substrate for palmitoylation, is conserved in most of the G-protein coupled receptors [O'Dowd, B. F. et al., *J. Biol. Chem.* 264:7564-7569 (1989)]. The short carboxyl tail, which terminates similar to the $D_2$ and $D_3$ receptor at Cys (387) [Bunzow, J. R. et al., *Nature* 336:783-787 (1988); Grandy, D. K. et al., *Proc. Natl. Acad. Sci. U.S.A.* 86:9762-9766 (1989); Dal Toso, R. et al., *EMBO J.* 8:4025-4034 (1989); Sokoloff, P. et al., *Nature* 347:146-151 (1990)], and the relative large 3rd cytoplasmic loop, are features observed in most receptors which interact with an isoform of the G protein.

EXAMPLE 5

Construction of an Mammalian DNA Expression Vector using Dopamine Receptor CDNA The SalI-PstI gene fragment (FIG. 1, the PstI site found in exon III after transmembrane domain V) was ligated to the corresponding PstI-EcoRI cDNA fragment isolated from the SK-N-MC cDNA. This construct was then cloned into the vector pCD-PS [Bonner et al., *Neuron* 1:403-410 (1988)]. This vector allows for the expression of the human $D_4$ receptor gene fore the SV40 promoter. Large quantities of the pCD-PS-$D_4$ construct plasmid were prepared using standard techniques. This plasmid was transfected into COS-7 cells by the calcium phosphate precipitation technique [Gorman et al., *Science* 221:551-553 (1983)]. Two days later membranes cells were harvested and analyzed as described in Example 6.

EXAMPLE 6

Analysis of Dopamine and Dopamine-Antagonist Binding of $D_4$ Dopamine Receptor Cells were harvested and homogenized using a teflon pestle in 50 mM Tris-HCl (pH 7.4 at 4° C.) buffer containing 5 mM EDTA, 1.5 mM $CaCl_2$, 5 mM $MgCl_2$, 5 mM KCl and 120 mM NaCl. Homogenates were centrifuged for 15 minutes at 39,000 g, and the resulting pellets resuspended in buffer at a concentration of 150-250 ug/ml. For saturation experiments, 0.25 ml aliquots of tissue homogenate were incubated in duplicate with increasing concentrations of [$^3$H]spiperone (70.3 Ci/mmol; 10-3000 pM final concentration) for 120 min at 22° C. in a total volume of 1 ml. The results of these experiments are shown in FIG. 4. For competition binding experiments, assays were initiated by the addition of 0.25 ml of membrane and incubated in duplicate with the concentrations of competing ligands indicated in FIG. 5 ($10^{-14}$ to $10^{-3}$M) and [$^3$H]spiperone (150-300 pM) for 120 min at 22° C.. Assays were terminated by rapid filtration through a Titertek cell harvester and filters subsequently monitored to quantitate radioactive tritium. For all experiments specific [$^3$H]spiperone binding was defined as that inhibited by 10 $\mu$M (+)sulpiride. Both saturation and competition binding data were analyzed by the non-linear least square curve-fitting program LIGAND run on a Digital Micro-PP-11. The human $D_4$ dopamine receptor displays the following pharmacological profile of inhibition of [$^3$H]spiperone binding in this assay: spiperone > eticlopride > clozapine (+)-butaclamol > raclopride > SCH23390 as shown in Table I.

---

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 388 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: 5'UTR
  ( B ) LOCATION: 1..103

( i x ) FEATURE:
  ( A ) NAME/KEY: exon
  ( B ) LOCATION: 104..388

( i x ) FEATURE:
  ( A ) NAME/KEY: CDS
  ( B ) LOCATION: 104..388

( x i ) SEQUENCE DESCRIPTION: SEQ ID NO:1:

| | | | | | |
|---|---|---|---|---|---|
| CGGGGGCGGG | ACCAGGGTCC | GGCCGGGGCG | TGCCCCCGGG | GAGGGACTCC | CCGGCTTGCC    60 |
| CCCCGGCGTT | GTCCGCGGTG | CTCAGCGCCC | GCCCGGGCGC | GCC ATG GGG AAC CGC    115 |
|            |            |            |            | Met Gly Asn Arg |
|            |            |            |            |   1             |

```
AGC ACC GCG GAC GCG GAC GGG CTG CTG GCT GGG CGC GGG CCG GCC GCG      163
Ser Thr Ala Asp Ala Asp Gly Leu Leu Ala Gly Arg Gly Pro Ala Ala
  5              10                  15                  20

GGG GCA TCT GCG GGG GCA TCT GCG GGG CTG GCT GGG CAG GGC GCG GCG      211
Gly Ala Ser Ala Gly Ala Ser Ala Gly Leu Ala Gly Gln Gly Ala Ala
                 25                  30                  35

GCG CTG GTG GGG GGC GTG CTG CTC ATC GGC GCG GTG CTC GCG GGG AAC      259
Ala Leu Val Gly Gly Val Leu Leu Ile Gly Ala Val Leu Ala Gly Asn
             40                  45                  50

TCG CTC GTG TGC GTG AGC GTG GCC ACC GAG CGC GCC CTG CAG ACG CCC      307
Ser Leu Val Cys Val Ser Val Ala Thr Glu Arg Ala Leu Gln Thr Pro
         55                  60                  65

ACC AAC TCC TTC ATC GTG AGC CTG GCG GCC GCC GAC CTC CTC CTC GCT      355
Thr Asn Ser Phe Ile Val Ser Leu Ala Ala Ala Asp Leu Leu Leu Ala
     70                  75                  80

CTC CTG GTG CTG CCG CTC TTC GTC TAC TCC GAG                          388
Leu Leu Val Leu Pro Leu Phe Val Tyr Ser Glu
 85                  90                  95
```

( 2 ) INFORMATION FOR SEQ ID NO:2:

( i ) SEQUENCE CHARACTERISTICS:
    ( A ) LENGTH: 95 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Gly Asn Arg Ser Thr Ala Asp Ala Asp Gly Leu Leu Ala Gly Arg
 1               5                  10                  15

Gly Arg Ala Ala Gly Ala Ser Ala Gly Ala Ser Ala Gly Leu Ala Gly
             20                  25                  30

Gln Gly Ala Ala Ala Leu Val Gly Gly Val Leu Leu Ile Gly Ala Val
             35                  40                  45

Leu Ala Gly Asn Ser Leu Val Cys Val Ser Val Ala Thr Glu Arg Ala
         50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu
                 85                  90                  95
```

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: intron
    ( B ) LOCATION: 1..20
    ( C ) IDENTIFICATION METHOD: experimental
    ( D ) OTHER INFORMATION: /partial
        / cons_splice=(5'site: YES, 3'site: NO)
        / evidence=EXPERIMENTAL
        / label=IntronI
        / note="This is the 5'sequence of an intron estimated to be 2.0 kilobases in length"

( x i ) SEQUENCE DESCRIPTION: SEQ ID NO:3:

```
GTGAGCCGCG TCCGGCCGCA                                           20
```

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: intron
    ( B ) LOCATION: 1..20
    ( C ) IDENTIFICATION METHOD: experimental
    ( D ) OTHER INFORMATION: /partial
        / cons_splice=(5'site: NO, 3'site: YES)
        / evidence=EXPERIMENTAL
        / label=IntronI
        / note="This is the 3'sequence of a intron estimated to be 2.0 kilobases in length."

( x i ) SEQUENCE DESCRIPTION: SEQ ID NO:4:

```
CCTGTGGTGT CGCCGCGCAG                                           20
```

( 2 ) INFORMATION FOR SEQ ID NO:5:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: exon
    ( B ) LOCATION: 1..113

( i x ) FEATURE:
    ( A ) NAME/KEY: CDS
    ( B ) LOCATION: 1..113

( x i ) SEQUENCE DESCRIPTION: SEQ ID NO:5:

```
GTC CAG GGT GGC GCG TGG CTG CTG AGC CCC CGC CTG TGC GAC GCC CTC    48
Val Gln Gly Gly Ala Trp Leu Leu Ser Pro Arg Leu Cys Asp Ala Leu
 1               5                  10                  15

ATG GCC ATG GAC GTC ATG CTG TGC ACC GCC TCC ATC TTC AAC CTG TGC    96
Met Ala Met Asp Val Met Leu Cys Thr Ala Ser Ile Phe Asn Leu Cys
             20                  25                  30

GCC ATC AGC GTG GAC AG                                            113
Ala Ile Ser Val Asp
         35
```

( 2 ) INFORMATION FOR SEQ ID NO:6:

( i ) SEQUENCE CHARACTERISTICS:
        ( A ) LENGTH: 37 amino acids (B) TYPE: amino acid
(D) TOPOLOGY: linear (ii) MOLECULE TYPE: protein (xi) SEQUENCE DESCRIPTION: SEQ ID NO:6:

```
Val Gln Gly Gly Ala Trp Leu Leu Ser Pro Arg Leu Cys Asp Ala Leu
 1               5                  10                  15

Met Ala Met Asp Val Met Leu Cys Thr Ala Ser Ile Phe Asn Leu Cys
                20                  25                  30

Ala Ile Ser Val Asp
            35
```

(2) INFORMATION FOR SEQ ID NO:7:

(i) SEQUENCE CHARACTERISTICS:
(A) LENGTH: 102 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..102
(C) IDENTIFICATION METHOD: experimental
(D) OTHER INFORMATION: /evidence=EXPERIMENTAL
/ label=IntronII (xi) SEQUENCE DESCRIPTION: SEQ ID NO:7:

```
GTGCGCCGCC CTCCCCGCCC GCGCCCGGC GCCCCGCGC CCCGCCCGCC GCCCTCACCG      60

CGGCCTGTGC GCTGTCCGGC GCCCCCTCGG CGCTCCCCGC AG                      102
```

(2) INFORMATION FOR SEQ ID NO:8:

(i) SEQUENCE CHARACTERISTICS:
(A) LENGTH: 409 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: exon
(B) LOCATION: 1..409

(ix) FEATURE:
(A) NAME/KEY: CDS
(B) LOCATION: 2..409

(xi) SEQUENCE DESCRIPTION: SEQ ID NO:8:

```
G TTC GTG GCC GTG GCC GTG CCG CTG CGC TAC AAC CGG CAG GGT GGG        46
  Phe Val Ala Val Ala Val Pro Leu Arg Tyr Asn Arg Gln Gly Gly
   1               5                  10                  15

AGC CGC CGG CAG CTG CTG CTC ATC GGC GCC ACG TGG CTG CTG TCC GCG     94
Ser Arg Arg Gln Leu Leu Leu Ile Gly Ala Thr Trp Leu Leu Ser Ala
                20                  25                  30

GCG GTG GCG GCG CCC GTA CTG TGC GGC CTC AAC GAC GTG CGC GGC CGC    142
Ala Val Ala Ala Pro Val Leu Cys Gly Leu Asn Asp Val Arg Gly Arg
                35                  40                  45

GAC CCC GCC GTG TGC CGC CTG GAG GAC CGC GAC TAC GTG GTC TAC TCG    190
Asp Pro Ala Val Cys Arg Leu Glu Asp Arg Asp Tyr Val Val Tyr Ser
            50                  55                  60

TCC GTG TGC TCC TTC TTC CTA CCC TGC CCG CTC ATG CTG CTG TAC        238
Ser Val Cys Ser Phe Phe Leu Pro Cys Pro Leu Met Leu Leu Tyr
        65                  70                  75

TGG GCC ACG TTC CGC GGC CTG CAG CGC TGG GAG GTG GCA CGT CGC GCC    286
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Trp | Ala | Thr | Phe | Arg | Gly | Leu | Gln | Arg | Trp | Glu | Val | Ala | Arg | Arg | Ala |     |
| 80  |     |     |     |     | 85  |     |     |     | 90  |     |     |     |     |     | 95  |     |
| AAG | CTG | CAC | GGC | CGC | GCG | CCC | CGC | CGA | CCC | AGC | GGC | CCT | GGC | CCG | CCT | 334 |
| Lys | Leu | His | Gly | Arg | Ala | Pro | Arg | Arg | Pro | Ser | Gly | Pro | Gly | Pro | Pro |     |
|     |     |     | 100 |     |     |     |     |     | 105 |     |     |     |     | 110 |     |     |
| TCC | CCC | ACG | CCA | CCC | GCG | CCC | CGC | CTC | CCC | CAG | GAC | CCC | TGC | GGC | CCC | 382 |
| Ser | Pro | Thr | Pro | Pro | Ala | Pro | Arg | Leu | Pro | Gln | Asp | Pro | Cys | Gly | Pro |     |
|     |     |     | 115 |     |     |     |     | 120 |     |     |     |     | 125 |     |     |     |
| GAC | TGT | GCG | CCC | CCC | GCG | CCC | GGC | CTC |     |     |     |     |     |     |     | 409 |
| Asp | Cys | Ala | Pro | Pro | Ala | Pro | Gly | Leu |     |     |     |     |     |     |     |     |
|     |     | 130 |     |     |     |     | 135 |     |     |     |     |     |     |     |     |     |

( 2 ) INFORMATION FOR SEQ ID NO:9:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

|     |     |     |     |     |     |     |     |     |     |     |     |     |     |     |     |
|-----|-----|-----|-----|-----|-----|-----|-----|-----|-----|-----|-----|-----|-----|-----|-----|
| Phe | Val | Ala | Val | Ala | Val | Pro | Leu | Arg | Tyr | Asn | Arg | Gln | Gly | Gly | Ser |
| 1   |     |     |     | 5   |     |     |     |     | 10  |     |     |     |     | 15  |     |
| Arg | Arg | Gln | Leu | Leu | Leu | Ile | Gly | Ala | Thr | Trp | Leu | Leu | Ser | Ala | Ala |
|     |     |     | 20  |     |     |     |     | 25  |     |     |     |     | 30  |     |     |
| Val | Ala | Ala | Pro | Val | Leu | Cys | Gly | Leu | Asn | Asp | Val | Arg | Gly | Arg | Asp |
|     |     | 35  |     |     |     |     | 40  |     |     |     |     | 45  |     |     |     |
| Pro | Ala | Val | Cys | Arg | Leu | Glu | Asp | Arg | Asp | Tyr | Val | Val | Tyr | Ser | Ser |
|     | 50  |     |     |     |     | 55  |     |     |     |     | 60  |     |     |     |     |
| Val | Cys | Ser | Phe | Phe | Leu | Pro | Cys | Pro | Leu | Met | Leu | Leu | Leu | Tyr | Trp |
| 65  |     |     |     |     | 70  |     |     |     |     | 75  |     |     |     |     | 80  |
| Ala | Thr | Phe | Arg | Gly | Leu | Gln | Arg | Trp | Glu | Val | Ala | Arg | Arg | Ala | Lys |
|     |     |     |     | 85  |     |     |     |     | 90  |     |     |     |     | 95  |     |
| Leu | His | Gly | Arg | Ala | Pro | Arg | Arg | Pro | Ser | Gly | Pro | Gly | Pro | Pro | Ser |
|     |     |     | 100 |     |     |     |     |     | 105 |     |     |     |     | 110 |     |
| Pro | Thr | Pro | Pro | Ala | Pro | Arg | Leu | Pro | Gln | Asp | Pro | Cys | Gly | Pro | Asp |
|     |     | 115 |     |     |     |     | 120 |     |     |     |     | 125 |     |     |     |
| Cys | Ala | Pro | Pro | Ala | Pro | Gly | Leu |     |     |     |     |     |     |     |     |
|     | 130 |     |     |     |     | 135 |     |     |     |     |     |     |     |     |     |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCCCCGGGGT CCCTGCGGCC           20

( 2 ) INFORMATION FOR SEQ ID NO:11:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CCTGTGCGCC CCCCGCGCCC GGCCTCCCCC AGGACCCCTG CGGCCCCGAC TGTGCGCCCC    60

CCGCGCCCGG CCT                                                      73
```

( 2 ) INFORMATION FOR SEQ ID NO:12:

( i ) SEQUENCE CHARACTERISTICS:
        ( A ) LENGTH: 155 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 1..155

( i x ) FEATURE:
        ( A ) NAME/KEY: CDS
        ( B ) LOCATION: 2..154

( x i ) SEQUENCE DESCRIPTION: SEQ ID NO:12:

```
C CCC CCG GAC CCC TGC GGC TCC AAC TGT GCT CCC CCC GAC GCC GTC AGA    49
  Pro Pro Asp Pro Cys Gly Ser Asn Cys Ala Pro Pro Asp Ala Val Arg
   1           5                  10                  15

GCC GCC GCG CTC CCA CCC CAG ACT CCA CCG CAG ACC CGC AGG AGG CGG     97
Ala Ala Ala Leu Pro Pro Gln Thr Pro Pro Gln Thr Arg Arg Arg Arg
            20                  25                  30

CGT GCC AAG ATC ACC GGC CGG GAG CGC AAG GCC ATG AGG GTC CTG CCG    145
Arg Ala Lys Ile Thr Gly Arg Glu Arg Lys Ala Met Arg Val Leu Pro
        35                  40                  45

GTG GTG GTC G                                                      155
Val Val Val
    50
```

( 2 ) INFORMATION FOR SEQ ID NO:13:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Pro Pro Asp Pro Cys Gly Ser Asn Cys Ala Pro Pro Asp Ala Val Arg
 1           5                  10                  15

Ala Ala Ala Leu Pro Pro Gln Thr Pro Pro Gln Thr Arg Arg Arg Arg
            20                  25                  30

Arg Ala Lys Ile Thr Gly Arg Glu Arg Lys Ala Met Arg Val Leu Pro
        35                  40                  45

Val Val Val
    50
```

( 2 ) INFORMATION FOR SEQ ID NO:14:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..94

( x i ) SEQUENCE DESCRIPTION: SEQ ID NO:14:

```
GTGGGTTCCT GTCCTGAGGG GCGGGGAGGA GAGGAGGGGG GGAGTACGAG GCCGGCTGGG        60

CGGGGGGCGC TAACGCGGCT CTCGGCGCCC CCAG                                   94
```

( 2 ) INFORMATION FOR SEQ ID NO:15:

( i ) SEQUENCE CHARACTERISTICS:
        ( A ) LENGTH: 328 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 1..328

( i x ) FEATURE:
        ( A ) NAME/KEY: CDS
        ( B ) LOCATION: 3..203

( i x ) FEATURE:
        ( A ) NAME/KEY: 3'UTR
        ( B ) LOCATION: 204..328

( i x ) FEATURE:
        ( A ) NAME/KEY: polyA_site
        ( B ) LOCATION: 304

( x i ) SEQUENCE DESCRIPTION: SEQ ID NO:15:

```
GG GCC TTC CTG CTG TGC TGG ACG CCC TTC TTC GTG GTG CAC ATC ACG         47
   Ala Phe Leu Leu Cys Trp Thr Pro Phe Phe Val Val His Ile Thr
    1           5                  10                  15

CAG GCG CTG TGT CCT GCC TGC TCC GTG CCC CCG CGG CTG GTC AGC GCC        95
Gln Ala Leu Cys Pro Ala Cys Ser Val Pro Pro Arg Leu Val Ser Ala
                20                  25                  30

GTC ACC TGG CTG GGC TAC GTC AAC AGC GCC CTC ACC CCC GTC ATC TAC       143
Val Thr Trp Leu Gly Tyr Val Asn Ser Ala Leu Thr Pro Val Ile Tyr
            35                  40                  45

ACT GTC TTC AAC GCC GAG TTC CGC AAC GTC TTC CGC AAG GCC CTG CGT       191
Thr Val Phe Asn Ala Glu Phe Arg Asn Val Phe Arg Lys Ala Leu Arg
        50                  55                  60

GCC TGC TGC TGAGCCGGGC ACCCCCGGAC GCCCCCGGC CTGATGGCCA                 240
Ala Cys Cys
        65

GGCCTCAGGG ACCAAGGAGA TGGGGAGGGC GCTTTGTAC GTTAATTAAA CAAATTCCTT       300

CCCAAACTCA GCTGTGAAGG CTCCTGGG                                         328
```

( 2 ) INFORMATION FOR SEQ ID NO:16:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ala Phe Leu Leu Cys Trp Thr Pro Phe Phe Val Val His Ile Thr Gln
 1               5                  10                  15

Ala Leu Cys Pro Ala Cys Ser Val Pro Pro Arg Leu Val Ser Ala Val
                20                  25                  30

Thr Trp Leu Gly Tyr Val Asn Ser Ala Leu Thr Pro Val Ile Tyr Thr
            35                  40                  45

Val Phe Asn Ala Glu Phe Arg Asn Val Phe Arg Lys Ala Leu Arg Ala
        50                  55                  60

Cys Cys
```

( 2 ) INFORMATION FOR SEQ ID NO:17:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:17:

```
Met Gly Asn Arg Ser Thr Ala Asp Ala Asp Gly Leu Leu Ala Gly Arg
  1               5                  10                  15

Gly Pro Ala Ala Gly Ala Ser Ala Gly Ala Ser Ala Gly Leu Ala Gly
                 20                  25                  30

Gln Gly Ala Ala Ala Leu Val Gly Gly Val Leu Leu Ile Gly Ala Val
                 35                  40                  45

Leu Ala Gly Asn Ser Leu Val Cys Val Ser Val Ala Thr Glu Arg Ala
     50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                 85                  90                  95

Gln Gly Gly Ala Trp Leu Leu Ser Pro Arg Leu Cys Asp Ala Leu Met
                100                 105                 110

Ala Met Asp Val Met Leu Cys Thr Ala Ser Ile Phe Asn Leu Cys Ala
                115                 120                 125

Ile Ser Val Asp Arg Phe Val Ala Val Ala Val Pro Leu Arg Tyr Asn
    130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
                180                 185                 190

Val Val Tyr Ser Ser Val Cys Ser Phe Phe Leu Pro Cys Pro Leu Met
                195                 200                 205

Leu Leu Leu Tyr Trp Ala Thr Phe Arg Gly Leu Gln Arg Trp Glu Val
    210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
                260                 265                 270

Pro Cys Gly Ser Asn Cys Ala Pro Pro Asp Ala Val Arg Ala Ala Ala
                275                 280                 285

Leu Pro Pro Gln Thr Pro Pro Gln Thr Arg Arg Arg Arg Arg Ala Lys
    290                 295                 300

Ile Thr Gly Arg Glu Arg Lys Ala Met Arg Val Leu Pro Val Val Val
305                 310                 315                 320

Gly Ala Phe Leu Leu Cys Trp Thr Pro Phe Phe Val Val His Ile Thr
                325                 330                 335

Gln Ala Leu Cys Pro Ala Cys Ser Val Pro Pro Arg Leu Val Ser Ala
                340                 345                 350
```

-continued

```
Val  Thr  Trp  Leu  Gly  Tyr  Val  Asn  Ser  Ala  Leu  Asn  Arg  Val  Ile  Tyr
          355                 360                      365

Thr  Val  Phe  Asn  Ala  Glu  Phe  Arg  Asn  Val  Phe  Arg  Lys  Ala  Leu  Arg
     370                 375                      380

Ala  Cys  Cys
385
```

( 2 ) INFORMATION FOR SEQ ID NO:18:

( i ) SEQUENCE CHARACTERISTICS:
        ( A ) LENGTH: 443 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:18:

```
Met  Asp  Pro  Leu  Asn  Leu  Ser  Trp  Tyr  Asp  Asp  Leu  Glu  Arg  Gln
1                  5                      10                      15

Asn  Trp  Ser  Arg  Pro  Phe  Asn  Gly  Ser  Asp  Gly  Lys  Ala  Asp  Arg  Pro
               20                      25                      30

His  Tyr  His  Tyr  Tyr  Ala  Thr  Leu  Leu  Thr  Leu  Leu  Ile  Ala  Val  Ile
          35                      40                      45

Val  Phe  Gly  Asn  Val  Leu  Val  Cys  Met  Ala  Val  Ser  Arg  Glu  Lys  Ala
     50                      55                      60

Leu  Gln  Thr  Thr  Thr  Asn  Tyr  Leu  Ile  Val  Ser  Leu  Ala  Val  Ala  Asp
65                       70                      75                      80

Leu  Leu  Val  Ala  Thr  Leu  Val  Met  Pro  Trp  Val  Val  Tyr  Leu  Glu  Val
                    85                      90                      95

Val  Gly  Glu  Trp  Lys  Phe  Ser  Arg  Ile  His  Cys  Asp  Ile  Phe  Val  Thr
                    100                     105                     110

Leu  Asp  Val  Met  Met  Cys  Thr  Ala  Ser  Ile  Leu  Asn  Leu  Cys  Ala  Ile
               115                     120                     125

Ser  Ile  Asp  Arg  Tyr  Thr  Ala  Val  Ala  Met  Pro  Met  Leu  Tyr  Asn  Thr
     130                     135                     140

Arg  Tyr  Ser  Ser  Lys  Arg  Val  Thr  Val  Met  Ile  Ser  Ile  Val  Trp
145                     150                     155                     160

Val  Leu  Ser  Phe  Thr  Ile  Ser  Cys  Pro  Leu  Leu  Phe  Gly  Leu  Asn  Asn
               165                     170                     175

Ala  Asp  Gln  Asn  Glu  Cys  Ile  Ile  Ala  Asn  Pro  Ala  Phe  Val  Val  Tyr
          180                     185                     190

Ser  Ser  Ile  Val  Ser  Phe  Tyr  Val  Pro  Phe  Ile  Val  Thr  Leu  Leu  Val
     195                     200                     205

Tyr  Ile  Lys  Ile  Tyr  Ile  Val  Leu  Arg  Arg  Arg  Lys  Arg  Val  Asn
210                     215                     220

Thr  Lys  Arg  Ser  Ser  Arg  Ala  Phe  Arg  Ala  His  Leu  Arg  Ala  Pro  Leu
225                     230                     235                     240

Lys  Gly  Asn  Cys  Thr  His  Pro  Glu  Asp  Met  Lys  Leu  Cys  Thr  Val  Ile
               245                     250                     255

Met  Lys  Ser  Asn  Gly  Ser  Phe  Pro  Val  Asn  Arg  Arg  Arg  Val  Asp  Ala
          260                     265                     270

Ala  Arg  Arg  Ala  Gln  Glu  Leu  Glu  Met  Glu  Met  Leu  Ser  Ser  Thr  Ser
     275                     280                     285

Pro  Pro  Glu  Arg  Thr  Arg  Tyr  Ser  Pro  Ile  Pro  Pro  Ser  His  His  Gln
     290                     295                     300

Leu  Thr  Leu  Pro  Asp  Pro  Ser  His  His  Gly  Leu  His  Ser  Thr  Pro  Asp
305                     310                     315                     320
```

|     |     |     |     |     |     |     |     |     |     |     |     |     |     |     |
|---|---|---|---|---|---|---|---|---|---|---|---|---|---|---|
| Ser | Pro | Ala | Lys | Pro | Glu | Lys | Asn | Gly | His | Ala | Lys | Asp | His | Pro | Lys |
|     |     |     |     | 325 |     |     |     | 330 |     |     |     |     |     | 335 |
| Ile | Ala | Lys | Ile | Phe | Glu | Ile | Gln | Thr | Met | Pro | Asn | Gly | Lys | Thr | Arg |
|     |     |     | 340 |     |     |     | 345 |     |     |     |     |     | 350 |     |     |
| Thr | Ser | Leu | Lys | Thr | Met | Ser | Arg | Arg | Lys | Leu | Ser | Gln | Gln | Lys | Glu |
|     |     | 355 |     |     |     |     | 360 |     |     |     |     | 365 |     |     |     |
| Lys | Lys | Ala | Thr | Gln | Met | Leu | Ala | Ile | Val | Leu | Gly | Val | Phe | Ile | Ile |
|     | 370 |     |     |     |     | 375 |     |     |     |     | 380 |     |     |     |     |
| Cys | Trp | Leu | Pro | Phe | Phe | Ile | Thr | His | Ile | Leu | Asn | Ile | His | Cys | Asp |
| 385 |     |     |     |     | 390 |     |     |     |     | 395 |     |     |     |     | 400 |
| Cys | Asn | Ile | Pro | Pro | Val | Leu | Tyr | Ser | Ala | Phe | Thr | Trp | Leu | Gly | Tyr |
|     |     |     |     | 405 |     |     |     |     | 410 |     |     |     |     | 415 |     |
| Val | Asn | Ser | Ala | Val | Asn | Pro | Ile | Ile | Tyr | Thr | Thr | Phe | Asn | Ile | Glu |
|     |     |     | 420 |     |     |     |     | 425 |     |     |     |     | 430 |     |     |
| Phe | Arg | Lys | Ala | Phe | Leu | Lys | Ile | Leu | His | Cys |     |     |     |     |     |
|     |     | 435 |     |     |     |     | 440 |     |     |     |     |     |     |     |     |

(2) INFORMATION FOR SEQ ID NO:19:

(i) SEQUENCE CHARACTERISTICS:
(A) LENGTH: 444 amino acids
(B) TYPE: amino acid
(D) TOPOLOGY: linear (ii) MOLECULE TYPE: protein (iii) HYPOTHETICAL: NO (xi) SEQUENCE DESCRIPTION: SEQ ID NO:19:

|     |     |     |     |     |     |     |     |     |     |     |     |     |     |     |     |
|---|---|---|---|---|---|---|---|---|---|---|---|---|---|---|---|
| Met | Asp | Pro | Leu | Asn | Leu | Ser | Trp | Tyr | Asp | Asp | Leu | Glu | Arg | Gln |
| 1   |     |     |     | 5   |     |     |     |     | 10  |     |     |     |     | 15  |
| Asn | Trp | Ser | Arg | Pro | Phe | Asn | Gly | Ser | Glu | Gly | Lys | Ala | Asp | Arg | Pro |
|     |     |     | 20  |     |     |     |     | 25  |     |     |     |     | 30  |     |     |
| His | Tyr | Asn | Tyr | Tyr | Ala | Met | Leu | Leu | Thr | Leu | Leu | Ile | Phe | Ile | Ile |
|     |     |     | 35  |     |     |     |     | 40  |     |     |     |     | 45  |     |     |
| Val | Phe | Gly | Asn | Val | Leu | Val | Cys | Met | Ala | Val | Ser | Arg | Glu | Lys | Ala |
|     | 50  |     |     |     |     | 55  |     |     |     |     | 60  |     |     |     |     |
| Leu | Gln | Thr | Thr | Thr | Asn | Tyr | Leu | Ile | Val | Ser | Leu | Ala | Val | Ala | Asp |
| 65  |     |     |     |     | 70  |     |     |     |     | 75  |     |     |     |     | 80  |
| Leu | Leu | Val | Ala | Thr | Leu | Val | Met | Pro | Trp | Val | Val | Tyr | Leu | Glu | Val |
|     |     |     |     | 85  |     |     |     |     | 90  |     |     |     |     | 95  |     |
| Val | Gly | Glu | Trp | Lys | Phe | Ser | Arg | Ile | His | Cys | Asp | Ile | Phe | Val | Thr |
|     |     |     | 100 |     |     |     |     | 105 |     |     |     |     | 110 |     |     |
| Leu | Asp | Val | Met | Met | Cys | Thr | Ala | Ser | Ile | Leu | Asn | Leu | Cys | Ala | Ile |
|     |     | 115 |     |     |     |     | 120 |     |     |     |     | 125 |     |     |     |
| Ser | Ile | Asp | Arg | Tyr | Thr | Ala | Val | Ala | Met | Pro | Met | Leu | Tyr | Asn | Thr |
|     | 130 |     |     |     |     | 135 |     |     |     |     | 140 |     |     |     |     |
| Arg | Tyr | Ser | Ser | Lys | Arg | Arg | Val | Thr | Val | Met | Ile | Ala | Ile | Val | Trp |
| 145 |     |     |     |     | 150 |     |     |     |     | 155 |     |     |     |     | 160 |
| Val | Leu | Ser | Phe | Thr | Ile | Ser | Cys | Pro | Leu | Leu | Phe | Gly | Ile | Asn | Asn |
|     |     |     |     | 165 |     |     |     |     | 170 |     |     |     |     | 175 |     |
| Thr | Asp | Gln | Asn | Glu | Cys | Ile | Ile | Ala | Asn | Pro | Ala | Phe | Val | Val | Tyr |
|     |     |     | 180 |     |     |     |     | 185 |     |     |     |     | 190 |     |     |
| Ser | Ser | Ile | Val | Ser | Phe | Tyr | Val | Pro | Phe | Ile | Val | Thr | Leu | Leu | Val |
|     |     | 195 |     |     |     |     | 200 |     |     |     |     | 205 |     |     |     |
| Tyr | Ile | Lys | Ile | Tyr | Ile | Val | Leu | Arg | Lys | Arg | Arg | Lys | Arg | Val | Asn |
|     | 210 |     |     |     |     | 215 |     |     |     |     | 220 |     |     |     |     |
| Thr | Lys | Arg | Ser | Ser | Arg | Ala | Phe | Arg | Ala | Asn | Leu | Lys | Thr | Pro | Leu |

```
                     225                        230                        235                        240
Lys  Gly  Asn  Cys  Thr  His  Pro  Glu  Asp  Met  Lys  Leu  Cys  Thr  Val  Ile
                    245                        250                        255

Met  Lys  Ser  Asn  Gly  Ser  Phe  Pro  Val  Asn  Arg  Arg  Arg  Met  Asp  Ala
                    260                        265                        270

Ala  Arg  Arg  Ala  Gln  Glu  Leu  Glu  Met  Glu  Met  Leu  Ser  Ser  Thr  Ser
                    275                        280                        285

Pro  Pro  Glu  Arg  Thr  Arg  Tyr  Ser  Pro  Ile  Pro  Pro  Ser  His  His  Gln
     290                        295                        300

Leu  Thr  Leu  Pro  Asp  Pro  Ser  His  His  Gly  Leu  His  Ser  Asn  Pro  Asp
305                      310                       315                       320

Ser  Pro  Ala  Lys  Pro  Glu  Lys  Asn  Gly  His  Ala  Lys  Ile  Val  Asn  Pro
               325                       330                            335

Arg  Ile  Ala  Lys  Phe  Phe  Glu  Ile  Gln  Thr  Met  Pro  Asn  Gly  Lys  Thr
               340                       345                       350

Arg  Thr  Ser  Leu  Lys  Thr  Met  Ser  Arg  Arg  Lys  Leu  Ser  Gln  Gln  Lys
          355                       360                       365

Glu  Lys  Lys  Ala  Thr  Gln  Met  Leu  Ala  Ile  Val  Leu  Gly  Val  Phe  Ile
     370                       375                       380

Ile  Cys  Trp  Leu  Pro  Phe  Phe  Ile  Thr  His  Ile  Leu  Asn  Ile  His  Cys
385                      390                       395                       400

Asp  Cys  Asn  Ile  Pro  Pro  Val  Leu  Tyr  Ser  Ala  Phe  Thr  Trp  Leu  Gly
               405                       410                            415

Tyr  Val  Asn  Ser  Ala  Val  Asn  Pro  Ile  Ile  Tyr  Thr  Thr  Phe  Asn  Ile
               420                       425                       430

Glu  Phe  Arg  Lys  Ala  Phe  Met  Lys  Ile  Leu  His  Cys
          435                       440
```

( 2 ) INFORMATION FOR SEQ ID NO:20:

( i ) SEQUENCE CHARACTERISTICS:
        ( A ) LENGTH: 444 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:20:

```
Met  Ala  Pro  Leu  Ser  Gln  Ile  Ser  Thr  His  Leu  Asn  Ser  Thr  Cys  Gly
1                   5                         10                        15

Ala  Glu  Asn  Ser  Thr  Gly  Val  Asn  Arg  Ala  Arg  Pro  His  Ala  Tyr  Tyr
               20                        25                        30

Ala  Leu  Ser  Tyr  Cys  Ala  Leu  Ile  Leu  Ala  Ile  Ile  Phe  Gly  Asn  Gly
          35                        40                        45

Leu  Val  Cys  Ala  Ala  Val  Ile  Arg  Glu  Arg  Ala  Leu  Gln  Thr  Thr  Thr
     50                        55                        60

Asn  Tyr  Leu  Val  Val  Ser  Leu  Ala  Val  Ala  Asp  Leu  Leu  Val  Ala  Thr
65                       70                        75                        80

Leu  Val  Met  Pro  Trp  Val  Val  Tyr  Leu  Glu  Val  Thr  Gly  Gly  Val  Trp
                    85                        90                        95

Asn  Phe  Ser  Arg  Ile  Cys  Cys  Asp  Val  Phe  Val  Thr  Leu  Asp  Val  Met
                    100                       105                       110

Met  Cys  Thr  Ala  Ser  Ile  Leu  Asn  Leu  Cys  Ala  Ile  Ser  Ile  Asp  Arg
                    115                       120                       125

Tyr  Thr  Ala  Val  Val  Met  Pro  Val  His  Tyr  Gln  His  Gly  Thr  Gly  Gln
               130                       135                       140
```

| | | | | | | | | | | | | | | |
|---|---|---|---|---|---|---|---|---|---|---|---|---|---|---|
| Ser 145 | Ser | Cys | Arg | Arg 150 | Val | Ala | Leu | Met | Ile 155 | Thr | Ala | Val | Trp | Val Leu 160 |
| Ala | Phe | Ala | Val | Ser 165 | Cys | Pro | Leu | Leu | Phe 170 | Gly | Phe | Asn | Thr | Thr Gly 175 |
| Asp | Pro | Ser | Ile 180 | Cys | Ser | Ile | Ser | Asn 185 | Pro | Asp | Phe | Val | Ile 190 | Tyr Ser |
| Ser | Val | Val 195 | Ser | Phe | Tyr | Val | Pro 200 | Phe | Gly | Val | Thr | Val 205 | Leu | Val Tyr |
| Ala | Arg 210 | Ile | Tyr | Ile | Val | Leu 215 | Arg | Gln | Arg | Gln | Arg 220 | Ile | Leu | Thr Arg |
| Gln 225 | Asn | Ser | Gln | Cys 230 | Ile | Ser | Ile | Arg | Pro 235 | Gly | Phe | Pro | Gln | Gln Ser 240 |
| Ser | Cys | Leu | Arg | Leu 245 | His | Pro | Ile | Arg | Gln 250 | Phe | Ser | Ile | Arg | Ala Arg 255 |
| Phe | Leu | Ser | Asp 260 | Ala | Thr | Gly | Gln | Met 265 | Glu | His | Ile | Glu | Asp 270 | Lys Gln |
| Tyr | Pro | Gln 275 | Lys | Cys | Gln | Asp | Pro 280 | Leu | Leu | Ser | His | Leu 285 | Gln | Pro Pro |
| Ser | Pro 290 | Gly | Gln | Thr | His | Gly 295 | Gly | Leu | Lys | Arg | Tyr 300 | Tyr | Ser | Ile Cys |
| Gln 305 | Asp | Thr | Ala | Leu | Arg 310 | His | Pro | Ser | Leu | Glu 315 | Gly | Gly | Ala | Gly Met 320 |
| Ser | Pro | Val | Glu | Arg 325 | Thr | Arg | Asn | Ser | Leu 330 | Ser | Pro | Thr | Met | Ala Pro 335 |
| Lys | Leu | Ser | Leu 340 | Glu | Val | Arg | Lys | Leu 345 | Ser | Asn | Gly | Arg | Leu 350 | Ser Thr |
| Ser | Leu | Arg 355 | Leu | Gly | Pro | Leu | Gln 360 | Pro | Arg | Gly | Val | Pro 365 | Leu | Arg Glu |
| Lys | Lys 370 | Ala | Thr | Gln | Met | Val 375 | Val | Ile | Val | Leu | Gly 380 | Ala | Phe | Ile Val |
| Cys 385 | Trp | Leu | Pro | Phe | Phe 390 | Leu | Thr | His | Val | Leu 395 | Asn | Thr | His | Cys Gln 400 |
| Ala | Cys | His | Val | Ser 405 | Pro | Glu | Leu | Tyr | Arg 410 | Ala | Thr | Thr | Trp | Leu Gly 415 |
| Tyr | Val | Asn | Ser 420 | Ala | Leu | Asn | Pro | Val 425 | Ile | Tyr | Thr | Thr | Phe 430 | Asn Val |
| Glu | Phe | Arg 435 | Lys | Ala | Phe | Leu | Lys 440 | Ile | Leu | Ser | Cys | | | |

( 2 ) INFORMATION FOR SEQ ID NO:21:

( i ) SEQUENCE CHARACTERISTICS:
      ( A ) LENGTH: 446 amino acids
      ( B ) TYPE: amino acid
      ( D ) TOPOLOGY: linear ( i i ) MOLECULE TYPE: protein ( i i i ) HYPOTHETICAL: NO ( x i ) SEQUENCE DESCRIPTION: SEQ ID NO:21:

| | | | | | | | | | | | | | | |
|---|---|---|---|---|---|---|---|---|---|---|---|---|---|---|
| Met 1 | Arg | Thr | Leu | Asn 5 | Thr | Ser | Ala | Met | Asp 10 | Gly | Thr | Gly | Leu | Val Val 15 |
| Glu | Arg | Asp | Phe 20 | Ser | Val | Arg | Ile | Leu 25 | Thr | Ala | Cys | Phe | Leu 30 | Ser Leu |
| Leu | Ile | Leu 35 | Ser | Thr | Leu | Leu | Gly 40 | Asn | Thr | Leu | Val | Cys 45 | Ala | Ala Val |
| Ile | Arg 50 | Phe | Arg | His | Leu | Arg 55 | Ser | Lys | Val | Thr | Asn 60 | Phe | Phe | Val Ile |

```
Ser  Leu  Ala  Val  Ser  Asp  Leu  Leu  Val  Ala  Val  Leu  Val  Met  Pro  Trp
65             70             75                  80

Lys  Ala  Val  Ala  Glu  Ile  Ala  Gly  Phe  Trp  Pro  Phe  Gly  Ser  Phe  Cys
               85             90                       95

Asn  Ile  Trp  Val  Ala  Phe  Asp  Ile  Met  Cys  Ser  Thr  Ala  Ser  Ile  Leu
               100            105                 110

Asn  Leu  Cys  Val  Ile  Ser  Val  Asp  Arg  Tyr  Trp  Ala  Ile  Ser  Ser  Pro
          115            120                      125

Phe  Arg  Tyr  Glu  Arg  Lys  Met  Thr  Pro  Lys  Ala  Ala  Phe  Ile  Leu  Ile
          130            135                 140

Ser  Val  Ala  Trp  Thr  Leu  Ser  Val  Leu  Ile  Ser  Phe  Ile  Pro  Val  Gln
145                      150                 155                      160

Leu  Ser  Trp  His  Lys  Ala  Lys  Pro  Thr  Ser  Pro  Ser  Asp  Gly  Asn  Ala
               165                      170                      175

Thr  Ser  Leu  Ala  Glu  Thr  Ile  Asp  Asn  Cys  Asp  Ser  Ser  Leu  Ser  Arg
               180                 185                           190

Thr  Tyr  Ala  Ile  Ser  Ser  Ser  Val  Ile  Ser  Phe  Tyr  Ile  Pro  Val  Ala
          195                      200                 205

Ile  Met  Ile  Val  Thr  Tyr  Thr  Arg  Ile  Tyr  Arg  Ile  Ala  Gln  Lys  Gln
210                      215                      220

Ile  Arg  Arg  Ile  Ala  Ala  Leu  Glu  Arg  Ala  Ala  Val  His  Ala  Lys  Asn
225                      230                 235                           240

Cys  Gln  Thr  Thr  Thr  Gly  Asn  Gly  Lys  Pro  Val  Glu  Cys  Ser  Gln  Pro
                    245                 250                      255

Glu  Ser  Ser  Phe  Lys  Met  Ser  Phe  Lys  Arg  Glu  Thr  Lys  Val  Leu  Lys
               260                 265                      270

Thr  Leu  Ser  Val  Ile  Met  Gly  Val  Phe  Val  Cys  Cys  Trp  Leu  Pro  Phe
          275                 280                      285

Phe  Ile  Leu  Asn  Cys  Ile  Leu  Pro  Phe  Cys  Gly  Ser  Gly  Glu  Thr  Gln
     290                 295                      300

Pro  Phe  Cys  Ile  Asp  Ser  Asn  Thr  Phe  Asp  Val  Phe  Val  Trp  Phe  Gly
305                      310                 315                      320

Trp  Ala  Asn  Ser  Ser  Leu  Asn  Pro  Ile  Ile  Tyr  Ala  Phe  Asn  Ala  Asp
               325                      330                      335

Phe  Arg  Lys  Ala  Phe  Ser  Thr  Leu  Leu  Gly  Cys  Tyr  Arg  Leu  Cys  Pro
          340                      345                 350

Ala  Thr  Asn  Asn  Ala  Ile  Glu  Thr  Val  Ser  Ile  Asn  Asn  Asn  Gly  Ala
          355                      360                 365

Ala  Met  Phe  Ser  Ser  His  His  Glu  Pro  Arg  Gly  Ser  Ile  Ser  Lys  Glu
     370                 375                      380

Cys  Asn  Leu  Val  Tyr  Leu  Ile  Pro  His  Ala  Val  Gly  Ser  Ser  Glu  Asp
385                      390                 395                           400

Leu  Lys  Lys  Glu  Glu  Ala  Ala  Gly  Ile  Ala  Arg  Pro  Leu  Glu  Lys  Leu
               405                      410                      415

Ser  Pro  Ala  Leu  Ser  Val  Ile  Leu  Asp  Tyr  Asp  Thr  Asp  Val  Ser  Leu
               420                 425                      430

Glu  Lys  Ile  Gln  Pro  Ile  Thr  Gln  Asn  Gly  Gln  His  Pro  Thr
          435                      440                 445
```

( 2 ) INFORMATION FOR SEQ ID NO:22:

( i ) SEQUENCE CHARACTERISTICS:
        ( A ) LENGTH: 446 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:22:

| Met | Ala | Pro | Asn | Thr | Ser | Thr | Met | Asp | Glu | Ala | Gly | Leu | Pro | Ala | Glu |
|---|---|---|---|---|---|---|---|---|---|---|---|---|---|---|---|
| 1 | | | | 5 | | | | | 10 | | | | | 15 | |

| Arg | Asp | Phe | Ser | Phe | Arg | Ile | Leu | Thr | Ala | Cys | Phe | Leu | Ser | Leu | Leu |
|---|---|---|---|---|---|---|---|---|---|---|---|---|---|---|---|
| | | | 20 | | | | | 25 | | | | | 30 | | |

| Ile | Leu | Ser | Thr | Leu | Leu | Gly | Asn | Thr | Leu | Val | Cys | Ala | Ala | Val | Ile |
|---|---|---|---|---|---|---|---|---|---|---|---|---|---|---|---|
| | | 35 | | | | | 40 | | | | | 45 | | | |

| Arg | Phe | Arg | His | Leu | Arg | Ser | Lys | Val | Thr | Asn | Phe | Phe | Val | Ile | Ser |
|---|---|---|---|---|---|---|---|---|---|---|---|---|---|---|---|
| | 50 | | | | | 55 | | | | | 60 | | | | |

| Leu | Ala | Val | Ser | Asp | Leu | Leu | Val | Ala | Val | Leu | Val | Met | Pro | Trp | Lys |
|---|---|---|---|---|---|---|---|---|---|---|---|---|---|---|---|
| 65 | | | | | 70 | | | | | 75 | | | | | 80 |

| Ala | Val | Ala | Glu | Ile | Ala | Gly | Phe | Trp | Pro | Phe | Gly | Ser | Phe | Cys | Asn |
|---|---|---|---|---|---|---|---|---|---|---|---|---|---|---|---|
| | | | | 85 | | | | | 90 | | | | | 95 | |

| Ile | Trp | Val | Ala | Phe | Asp | Ile | Met | Cys | Ser | Thr | Ala | Ser | Ile | Leu | Asn |
|---|---|---|---|---|---|---|---|---|---|---|---|---|---|---|---|
| | | | 100 | | | | | 105 | | | | | 110 | | |

| Leu | Cys | Val | Ile | Ser | Val | Asp | Arg | Tyr | Trp | Ala | Ile | Ser | Ser | Pro | Phe |
|---|---|---|---|---|---|---|---|---|---|---|---|---|---|---|---|
| | | 115 | | | | | 120 | | | | | 125 | | | |

| Gln | Tyr | Glu | Arg | Lys | Met | Thr | Pro | Lys | Ala | Ala | Phe | Ile | Leu | Ile | Ser |
|---|---|---|---|---|---|---|---|---|---|---|---|---|---|---|---|
| | 130 | | | | | 135 | | | | | 140 | | | | |

| Val | Ala | Trp | Thr | Leu | Ser | Val | Leu | Ile | Ser | Phe | Ile | Pro | Val | Gln | Leu |
|---|---|---|---|---|---|---|---|---|---|---|---|---|---|---|---|
| 145 | | | | | 150 | | | | | 155 | | | | | 160 |

| Ser | Trp | His | Lys | Ala | Lys | Pro | Thr | Trp | Pro | Leu | Asp | Gly | Asn | Phe | Thr |
|---|---|---|---|---|---|---|---|---|---|---|---|---|---|---|---|
| | | | | 165 | | | | | 170 | | | | | 175 | |

| Ser | Leu | Glu | Asp | Thr | Glu | Asp | Asp | Asn | Cys | Asp | Thr | Arg | Leu | Ser | Arg |
|---|---|---|---|---|---|---|---|---|---|---|---|---|---|---|---|
| | | | 180 | | | | | 185 | | | | | 190 | | |

| Thr | Tyr | Ala | Ile | Ser | Ser | Ser | Leu | Ile | Ser | Phe | Tyr | Ile | Pro | Val | Ala |
|---|---|---|---|---|---|---|---|---|---|---|---|---|---|---|---|
| | | 195 | | | | | 200 | | | | | 205 | | | |

| Ile | Met | Ile | Val | Thr | Tyr | Thr | Ser | Ile | Tyr | Arg | Ile | Ala | Gln | Leu | Gln |
|---|---|---|---|---|---|---|---|---|---|---|---|---|---|---|---|
| | 210 | | | | | 215 | | | | | 220 | | | | |

| Ile | Arg | Arg | Ile | Ser | Ala | Leu | Glu | Arg | Ala | Ala | Val | His | Ala | Lys | Asn |
|---|---|---|---|---|---|---|---|---|---|---|---|---|---|---|---|
| 225 | | | | | 230 | | | | | 235 | | | | | 240 |

| Cys | Gln | Thr | Thr | Ala | Gly | Asn | Gly | Asn | Pro | Val | Glu | Cys | Ala | Gln | Ser |
|---|---|---|---|---|---|---|---|---|---|---|---|---|---|---|---|
| | | | | 245 | | | | | 250 | | | | | 255 | |

| Glu | Ser | Ser | Phe | Lys | Met | Ser | Phe | Lys | Arg | Glu | Thr | Lys | Val | Leu | Lys |
|---|---|---|---|---|---|---|---|---|---|---|---|---|---|---|---|
| | | | 260 | | | | | 265 | | | | | 270 | | |

| Thr | Leu | Ser | Val | Ile | Met | Gly | Val | Phe | Val | Cys | Cys | Trp | Leu | Pro | Phe |
|---|---|---|---|---|---|---|---|---|---|---|---|---|---|---|---|
| | | 275 | | | | | 280 | | | | | 285 | | | |

| Phe | Ile | Ser | Asn | Cys | Met | Val | Pro | Phe | Cys | Gly | Ser | Glu | Glu | Thr | Gln |
|---|---|---|---|---|---|---|---|---|---|---|---|---|---|---|---|
| | 290 | | | | | 295 | | | | | 300 | | | | |

| Pro | Phe | Cys | Ile | Asp | Ser | Ile | Thr | Phe | Asp | Val | Phe | Val | Trp | Phe | Gly |
|---|---|---|---|---|---|---|---|---|---|---|---|---|---|---|---|
| 305 | | | | | 310 | | | | | 315 | | | | | 320 |

| Trp | Ala | Asn | Ser | Ser | Leu | Asn | Pro | Ile | Ile | Tyr | Ala | Phe | Asn | Ala | Asp |
|---|---|---|---|---|---|---|---|---|---|---|---|---|---|---|---|
| | | | | 325 | | | | | 330 | | | | | 335 | |

| Phe | Gln | Lys | Ala | Phe | Ser | Thr | Leu | Leu | Gly | Cys | Tyr | Arg | Leu | Cys | Pro |
|---|---|---|---|---|---|---|---|---|---|---|---|---|---|---|---|
| | | | 340 | | | | | 345 | | | | | 350 | | |

| Thr | Thr | Asn | Asn | Ala | Ile | Glu | Thr | Val | Ser | Ile | Asn | Asn | Asn | Gly | Ala |
|---|---|---|---|---|---|---|---|---|---|---|---|---|---|---|---|
| | | 355 | | | | | 360 | | | | | 365 | | | |

| Val | Val | Phe | Ser | Ser | His | His | Glu | Pro | Arg | Gly | Ser | Ile | Ser | Lys | Asp |
|---|---|---|---|---|---|---|---|---|---|---|---|---|---|---|---|
| | 370 | | | | | 375 | | | | | 380 | | | | |

| Cys | Asn | Leu | Val | Tyr | Leu | Ile | Pro | His | Ala | Val | Gly | Ser | Ser | Glu | Asp |
|---|---|---|---|---|---|---|---|---|---|---|---|---|---|---|---|
| 385 | | | | | 390 | | | | | 395 | | | | | 400 |

| Leu | Lys | Lys | Glu | Glu | Ala | Gly | Gly | Ile | Ala | Lys | Pro | Leu | Glu | Lys | Leu |
|---|---|---|---|---|---|---|---|---|---|---|---|---|---|---|---|
| | | | 405 | | | | | 410 | | | | | 415 | | |

-continued

```
Ser Pro Ala Leu Ser Val Ile Leu Asp Tyr Asp Thr Asp Val Ser Leu
            420             425             430

Glu Lys Ile Gln Pro Val Thr His Ser Gly Gln His Ser Thr
        435             440             445
```

| Dopamine Receptor Drug Dissociation Constants | | | |
|---|---|---|---|
| | $D_2$(long) $K_i$ | $D_4 K_i$ | $D_2 K_i / D_4 K_i$ |
| Dopamine Antagonists | | | |
| Butaclamol-(+) | 0.9 H | 36 | 0.03 |
| Chlorpromazine | 2.8 R | 23 | 0.12 |
| Chlorpromazine | 1.5 H | 23 | 0.07 |
| Clozapine | ~130 T | 11 | 11.8 |
| Clozapine | 56 R | 11 | 5.1 |
| Clozapine | 158 H | 11 | 15.3 |
| Eticlopride | 0.09 T | 0.52 | 0.17 |
| Fluphenazine | 0.5 T | 42 | 0.01 |
| Haloperidol | 0.5 R | 4.5 | 0.11 |
| Haloperidol | 0.8 R | 4.5 | 0.18 |
| Haloperidol | 1 H | 4.5 | 0.22 |
| Ketanserin | 192 T | 147 | 1.31 |
| Octoclothepin-S | 1.5 T | 0.8 | 1.58 |
| Octoclothepin-R | 13.5 T | 1.9 | 7.11 |
| Pimozide | 2.4 R | 25 | 0.1 |
| Raclopride | 1.8 R | 253 | 0.01 |
| Raclopride | 1.6 H | 253 | 0.01 |
| *Raclopride | 3.2 H | 253 | 0.01 |
| Remoxipride | ~300 T | 2730 | 0.11 |
| SCH 23390 | 913 H | 1960 | 0.47 |
| Spiperone | 0.069 H | 0.06 | 1.15 |
| Spiperone | 0.053 H | 0.06 | 0.88 |
| *Spiperone | 0.05 H | 0.06 | 0.83 |
| *Spiperone | 0.09 H | 0.06 | 1.5 |
| Sulpiride-S | 9.2 R | 63 | 0.02 |
| Sulpiride-S | 4.8 R | 63 | 0.08 |
| Sulpiride-S | 46 H | 63 | 0.73 |
| Sulpiride-S | 15.9 H | 63 | 0.25 |
| Thioproperazine | 0.21 R | 53 | 0.004 |
| Thioridazine | 3.3 H | 12 | 0.28 |
| Trifluoperazine | 1.2 T | 2.2 | 0.55 |
| YM-09151-2 | 0.06 T | 0.11 | 0.55 |
| *YM-09151-2 | 0.09 H | 0.11 | 0.82 |

-continued

| Dopamine Receptor Drug Dissociation Constants | | | |
|---|---|---|---|
| | $D_2$(long) $K_i$ | $D_4 K_i$ | $D_2 K_i / D_4 K_i$ |
| Dopamine Agonists | | | |
| ADTN-(±) | 1.7 T | 33.7 | |
| Apomorphine | ~2 T | 3.3 | |
| Apomorphine | 24 R | | |
| Bromocriptine | 5.3 R | 128 | |
| Bromocriptine | 14 H | | |
| Dopamine | 7.5 T | 18.6 | |
| Dopamine | 2.8 R | | |
| Dopamine | 474 R | | |
| Dopamine + G | 1705 R | 49 | |
| Ergocriptine-S | 0.4 T | 55 | |
| Fencidopam | 2.8 T | 420 | |
| N-0437 | 0.7 T | 93 | |
| (−) Noradrenaline | ~6,000 T | ~6,000 | |
| NPA | 0.4 T | 5.5 | |
| PHNO-(+) | 1.2 T | 42 | |
| Quinpirole(±) | 576 R | | |
| Quinpirole(−) | 4.8 T | 17 | |
| Serotonin | ~10,000 T | ~8,000 | |
| SKF-38393 | 157 T | 1600 | |
| SKF-38393 | 9560 R | | |

* = [$^3$H]-labeled; T = tissue homogenate; R = rat $D_2$; H = human $D_2$

What we claim is:

1. An isolated and purified nucleic acid having a nucleotide residue sequence which encodes human $D_4$ dopamine receptor where said human $D_4$ dopamine receptor has an amino acid residue sequence of SEQ ID No: 17 as set forth in FIG. 3.

2. A recombinant expression for comprising the nucleic acid of claim 1 wherein the vector expresses the human $D_4$ dopamine receptor in a transformed eukaryotic cell culture.

3. A eukaryotic cell culture transformed with the expression vector of claim 1, wherein the transformed eukaryotic cell culture expresses the human dopamine receptor $D_4$.

* * * * *